(12) United States Patent
Clarke et al.

(10) Patent No.: US 8,287,878 B2
(45) Date of Patent: Oct. 16, 2012

(54) SYNERGISTIC ATTENUATION OF VESICULAR STOMATITIS VIRUS, VECTORS THEREOF AND IMMUNOGENIC COMPOSITIONS THEREOF

(75) Inventors: David Kirkwood Clarke, Chester, NY (US); Roger Michael Hendry, Warwick, NY (US); Stephen A. Udem, New York, NY (US); Christopher Lee Parks, Boonton, NJ (US)

(73) Assignee: Wyeth LLC, Madison, NJ (US)

( * ) Notice: Subject to any disclaimer, the term of this patent is extended or adjusted under 35 U.S.C. 154(b) by 1022 days.

(21) Appl. No.: 11/547,236

(22) PCT Filed: Apr. 5, 2005

(86) PCT No.: PCT/US2005/011499
§ 371 (c)(1),
(2), (4) Date: Oct. 3, 2006

(87) PCT Pub. No.: WO2005/098009
PCT Pub. Date: Oct. 20, 2005

(65) Prior Publication Data
US 2007/0218078 A1  Sep. 20, 2007

Related U.S. Application Data

(60) Provisional application No. 60/561,214, filed on Apr. 9, 2004, provisional application No. 60/644,902, filed on Jan. 19, 2005.

(51) Int. Cl.
*A61K 39/12* (2006.01)
*C12N 7/01* (2006.01)
(52) U.S. Cl. ............... 424/199.1; 435/235.1; 435/320.1
(58) Field of Classification Search .................... None
See application file for complete search history.

(56) References Cited

U.S. PATENT DOCUMENTS

| | | | |
|---|---|---|---|
| 5,258,454 A | 11/1993 | Berg et al. | |
| 5,556,747 A | 9/1996 | Kumar | |
| 5,789,166 A | 8/1998 | Bauer et al. | |
| 5,817,879 A | 10/1998 | Hirschmann et al. | |
| 6,033,886 A * | 3/2000 | Conzelmann | 424/205.1 |
| 6,168,943 B1 | 1/2001 | Rose | |
| 6,391,548 B1 | 5/2002 | Bauer et al. | |
| 6,596,529 B1 * | 7/2003 | Wertz et al. | 435/236 |
| 6,673,572 B2 | 1/2004 | Parks et al. | |
| 2003/0099671 A1 | 5/2003 | Fu | |

FOREIGN PATENT DOCUMENTS

| | | |
|---|---|---|
| WO | WO-98/50529 | 11/1998 |
| WO | WO-2004/113517 | 12/2004 |

OTHER PUBLICATIONS

Jayakar et al. (Journal of Virology, 2000, vol. 74, p. 9818-9827 in IDS of Dec. 13, 2006.*
Preble et al. Infection and Immunity, 1980, vol. 29, p. 744-757.*
Schnell et al. EMBO, 1998, vol. 17, p. 1289-1296 in IDS of Dec. 13, 2006.*
Jeetendra et al. (Journal of Virology, 2002, vol. 76, p. 12300-12311).*
Jayakar et al. (Journal of Virology, 2000, vol. 74, p. 9818-9827).*
Rose et al. (Cell, 2001, vol. 106, p. 539-549).*
Ahmed et al., "Identification of a Consensus Mutation in M Protein of Vesicular Stomatitis Virus from Persistently Infected Cells that Affects Inhibition of Host-directed Gene Expression", Virology, 237(1): 378-88 (1997).
Atkinson et al., "The Resurgence of Measles in the United States", Annu. Rev. Med., 43:451-463 (1992).
Ball et al., Phenotypic Consequences of Rearranging the P, M. and G Genes of Vesicular Stomatitis Virus, J. Virol., 73(6):4705-4712 (Jun. 1999).
Bellini et al., "Genetic Diversity of Wild-Type Measles: Implications for Global Measles Elimination Programs", Emerging Infectious Diseases, 4:29-35 (Jan.-Mar. 1998).
Canto et al., "Status Spongiosus Resulting from Intracerebral Infection of Mice with Temperature-Sensitive Mutants of Vesicular Stomatitis Virus", Br. J. exp. Path., 57:321-330 (1976).
Collins et al., "Rational Design of Live-Attenuated Recombinant Vaccine Virus for Human Respiratory Syncytial Virus by Reverse Genetics", Adv. Virus. Res., 54:423-451 (1999).
Collins et al., "Respiratory Syncytial Virus", Chapter 45, in "Field's Virology", 4th Edition, Lippincott-Raven, 1443-1475 (2001).
Cutts et al., "Success and Failures in Measles Control" J. Infect. Dis., 170:S32-S41 (Nov. 1994).
Evans et al., "Temperature-Sensitive Mutants of Complementation Group E of Vesicular Stomatitis Virus New Jersey serotype Possess Altered NS Polypeptides", J. Virol., 31(2):325-333 (Aug. 1979).
Finke et al., "Ambisense Gene Expression from Recombinant Rabies Virus: Random Packaging of Positive- and Negative-Strand Ribonucleoprotein Complexes into Rabies Virions", J. Virol.. 71:7281-7288 (Oct. 1997).
Finke et al., "Virus Promoters Determine Interference by Defective RNAs: Selective Amplification of Mini-RNA Vectors and Rescue from cDNA by a 3' Copy-Back Ambisense Rabies Virus", J. Virol., 73:3818-3825 (May 1999).
Finke et al., "Replication Strategies of Rabies Virus" Virus Research, 111(2): 120-131 (Aug. 2005).
Flamand et al., "The Homologies of Spontaneous and Temperature-Sensitive Mutants of Vesicular Stomatitis Virus Isolated in Chick Embryos and BHK-21 Cells", J. Gen. Virol., 11:81-85 (1971).
Flamand et at., "Primary In Vivo Transcription of Vesicular Stomatitis Virus and Temperature-Sensitive Mutants of Five Vesicular Stomatitis Virus Complementation Groups", J. of Virol., 12(6):1238-1252 (Dec. 1973).
Flanagan et al., "Rearrangement of the Genes of Vesicular Stomatitis Virus Eliminates Clinical Disease in the Natural Host: A New Strategy for Vaccine Development", J. Virol., 75:6107-6114 (Jul. 2001).
Flanagan et al., "Vesicular Stomatitis Viruses with Rearranged Genomes have Altered Invasiveness and Neiropathogenesis in Mice" J. Virol., 77(10): 5740-5748 (May 2003).

(Continued)

*Primary Examiner* — Shanon A Foley
(74) *Attorney, Agent, or Firm* — Lynn D. Apelgren

(57) ABSTRACT

The present invention broadly relates to the synergistic attenuation of vesicular stomatitis virus (VSV). More particularly, the invention relates to the identification of combined mutation classes which synergistically attenuate the pathogenicity of VSV vectors in mammals and immunogenic compositions thereof.

17 Claims, 3 Drawing Sheets

OTHER PUBLICATIONS

Fredericksen et al., "Attenuation of Recombinant Vesicular Stomatitis Viruses Encoding Mutant Glycoproteins Demonstrate a Critical Role for Maintaining a High pH Threshold for Membrane Fusion in Viral Fitness", Virology, 240: 349-58 (1998).
Gallione et al., "Nucleotide Sequences of the mRNA's Encoding the Vesicular Stomatitis Virus N and NS Proteins", J. Viol., 39:529-535 (Aug. 1981).
Gopalakrishna et al., "Sequence Alterations in Temperature-Sensitive M-Protein Mutants (Complementation Group III) of Vesicular Stomatitis Virus", J. Virol., 56(3):655-659 (Dec. 1985).
Griffin, "Measles Virus", Chapter 44, in Field's Virology, $4^{th}$ Edition, Lippincott-Raven, 1401-1442 (2001).
Haglund et al., "Expression of Human Immunodeficiency Virus Type 1 Gag Protein Precursors and Envelope Proteins from a Vesicular Stomatitis Virus Recombinant: High-Level Production of Virus-Like Particles Containing HIV Envelope" Virology, 268(1): 112-131 (Mar. 1, 2000).
Harty et al., "A Proline-Rich Motif with the Matrix Protein of Vesicular Stomatitis Virus and Rabies Virus Interacts with WW Domains of Cellular Proteins: Implications for Viral Budding", J. Virol., 73(4):2921-2929 (Apr. 1999).
Holloway et al., "Isolation and Characterization of Temperature-Sensitive Mutants of Vesicular Stomatitis Virus", Virol., 42(4):917-926 (1970).
Irie et al., "Functional Analysis of Late-Budding Domain Activity Associated with the PSAP Motif within the Vesicular Stomatitis Virus M Protein", J. Virol., 78(14):7823-7827 (Jul. 2004).
Jayakar et al., Mutations in the PPPY Motif of Vesicular Stomatitis Virus Matrix Protein Reduce Virus Budding by Inhibiting a Late Step in Virion Release, J. Virol., 74(21):9818-9827 (Nov. 2000).
Jayakar et al., "Identification of Two Additional Translation Products from the Matrix (M) Gene that Contribute to Vesicular Stomatitis Virus Cytopathology" J. Virol., 76(16):8011-8018 (Aug. 2002).
Jeetendra et al., "The Membrane-Proximal Domain of Vesicular Stomatitis Virus G Protein Functions as a membrane Fusion Potentiator and Can Induce Hemifusion", J. Virol., 76(23):12300-12311 (Dec. 2002).
Jeetendra et al., The Membrane-Proximal Region of Vesicular Stomatitis Virus Glycoprotein G Ectodomain is Critical for Fusion and virus Infectivity, J. Virol., 77(23): 12807-12818 (Dec. 2003).
Kahn et al., "Replication-Competent or Attenuated Nonpropagating Vesicular Stomatitis Viruses Expressing Respiratory Syncytial Virus (RSV) Antigens Protect Mice Against RSV Challenge", J. Virol., 75(22): 11079-11087 (Nov. 2001).
Kapikian et al., "An Epidemiologic Study of Altered Clinical Reactivity to Respiratory Syncytial (RS) Virus Infection in Children Previously Vaccinated with an Inactivated RS Virus Vaccine.", Am. J. Epidemiol. 4: 405-21 (1969).
Kim et al., "Respiratory Syncytial Virus Disease in Infants Despite Prior Administration of Antigenic Inactivated Vaccine", Am. J. Epidemiol. 4:422-34 (1969).
Li et al., "Site-specific Mutations in Vectors that Express Antigenic and Temperature-Sensitive Phenotypes of the M Gene of Vesicular Stomatitis Virus", J. Virol.,62(10):3729-3737 (Oct. 1988).
Lundh et al., "Non-Lethal Infection of Aminergic Reticular Core Neurons: Age-Dependent Spread of ts Mutant Vesicular Stomatitis Virus from the Nose", J. Neuropathology and Exp. Neurology, 47(5):497-506 (Sep. 1988).
Morita et al., "Phenotypic Revertants of Temperature-Sensitive M Protein Mutants of Vesicular Stomatitis Virus: Sequence Analysis and Functional Characterization", J. Virol., 61(2):256-263 (Feb. 1987).
Pringle et al., "Isolation and Characterization of Temperature-Sensitive Mutants of Vesicular Stomatitis Virus, New Jersey Serotype", J. Virol., 8(6):836-841 (Dec. 1971).
Pringle et al., "Enhanced Mutability Associated with a Temperature-Sensitive Mutant of Vesicular Stomatitis Virus", J. Virol., 39(2):377-389 (Aug. 1981).
Pringle, "Genetic Characteristics of Conditional Lethal Mutants of Vesicular Stomatitis Virus Induced by 5-Fluorouracil, 5-Azacytidine, and Ethyl Methane Sulfonate", J. Virol., 5(5):559-567 (May 1970).
Printz et al., "Temperature-Sensitive Mutants of Vesicular Stomatitis Virus: Synthesis of Virus Specific Proteins", J. of Virol., 7(5):651-662 (May 1971).
Publicover et al., "Characterization of Nonpathogenic, Live, Viral Vaccine Vector Inducing Potent Cellular Immune Responses" J. Virol., 78(17):9317-9324 (Sep. 2004).
Rabinowitz et al., "The Uncoupled Relationship Between the Temperature-Sensitivity and Neurovirulence in Mice of Mutants of Vesicular Stomatitis Virus", J. Gen. Virol, 35:237-249 (May 1977).
Rabinowitz et al, "Comparison of Central Nervous System Disease Produced by Wild-Type and Temperature-Sensitive Mutants of Vesicular Stomatitis Virus", Infection and Immunity, 13(4):1242-1249 (Apr. 1976).
Roberts et al., "Attenuated Vesicular Stomatitis Viruses as Vaccine Vectors", J. Virol., 73:3723-3732 (May 1999).
Roberts, "Vaccination with a Recombinant Vesicular Stomatitis Virus Expressing an Influenza Virus Hemagglutinin Provides Complete Protection from Influenza Virus Challenge", J. Virol., 72(6): 4704-4711 (Jun. 1998).
Robison et al., "The Membrane-Proximal Stem Region of Vesicular Stomatitis Virus G Protein Confers Efficient Virus Assembly", J. Virol., 74(5):2239-2246 (2000).
Rose et al., "Nucleotide Sequences of the mRNA's Encoding the Vesicular Stomatitis Virus G and M Proteins Determined from cDNA Clones Containing the Complete Coding Regions", J. Virol., 39:519-528 (Aug. 1981).
Rose et al., "Rhabdovirus Genomes and Their Products" Chapter 4, In The Rhabdoviruses, Wagner, ed., Press, New York, NY:129-166 (1987).
Rose et al., "Glycoprotein Exchange Vectors Based on Vesicular Stomatitis Virus Allow Effective Boosting and Generation of Neutralizing Antibodies to a Primary Isolate of Human Immunodeficiency Virus Type 1", J. Virol., 74(23):10903-10 (Dec. 2000).
Rose et al., "An Effective Aids Vaccine Based on Live Attenuated Vesicular Stomatitis Virus Recombinants" Cell, 106(5):549-549 (Sep. 7, 2001).
Schlehuber et al., "Vesicular Stomatitis Virus (VSV) Recombinants Expressing the HIV-1 2F5 Epitope Within the VSV G Proteins", Abstract No. 321, AIDS Vaccine, New York, NY (Sep. 2003).
Schlereth et al., "Successful Mucosal Immunization of Cotton Rats in the Presence of measles-Specific Antibodies Depends on Degree of Attenuation of Vaccine Vector and Virus Dose", J. General. Virol., 84:2145-2151 (2003).
Schlereth et al. , "Successful Vaccine-Induced Seroconversion by Single-Dose immunization in the Presence of Measles Virus-Specific Material Antibodies", J. Virology, 74: 4652-4657 (May 2000).
Schnell et al., "Requirement for a Non-Specific Glycoprotein Cytoplasmic Domain Sequence to Drive Efficient Budding of Vesicular Stomatitis Virus", EMBO J., 17(5):1289-1296 (1998).
Schnell et al., "Foreign Glycoproteins Expressed from Recombinant Vesicular Stomatitis Viruses are Incorporated Efficiently into Virus Particles", PNAS U S A, 93:11359-11365 (Oct. 1996).
Schubert et al., "Expression of a cDNA Encoding a Functional 241-Dilodalton Vesicular Stomatitis Virus RNA Polymerase", PNAS, USA, 82(23): 7984 (Dec. 1985).
Wagner, "Pathogenicity and Immunogenicity for Mice of Temperature-Sensitive Mutants of Vesicular Stomatitis Virus", Infection and Immunity, 10(2):309- 315 (Aug. 1974).
Wertz et al., "Gene Rearrangement Attenuates Expression and Lethality of a Nonsegmented Negative Strand RNA Virus", PNAS USA, 95:3501-3506 (Mar. 1998).
Vandepol et al., Genbank Accession No. X04452 (Feb. 23, 1987).
Gill et al., Genbank Accession No. M14553 (Feb. 23, 1987).

* cited by examiner

SYNERGISTIC ATTENUATION OF
VESICULAR STOMATITIS VIRUS, VECTORS
THEREOF AND IMMUNOGENIC
COMPOSITIONS THEREOF

This application is a 371 of International Patent Application No. PCT/US2005/011499, filed Apr. 5, 2005, which claims the benefit of the priorities of U.S. Provisional Patent Application No. 60/644,902, filed Jan. 19, 2005 and U.S. Provisional Patent Application No. 60/561,214, filed Apr. 9, 2004, both abandoned.

FIELD OF THE INVENTION

The present invention generally relates to the fields of virology, microbiology, infectious disease and immunology. More particularly, the invention relates to the synergistic attenuation of vesicular stomatitis virus and vectors thereof, by combination of different classes of mutation.

BACKGROUND OF THE INVENTION

Vesicular stomatitis virus (VSV), a member of the Rhabdoviridae family, has a non-segmented, negative-sense, single-stranded RNA genome. Its eleven kb genome has five genes which encode five structural proteins of the virus; the nucleocapsid protein (N), which is required in stoichiometric amounts for encapsidation of the replicated RNA; the phosphoprotein (P), which is a cofactor of the RNA-dependent RNA polymerase (L); the matrix protein (M) and the attachment glycoprotein (G) (e.g., see Gallione et al. 1981, Rose and Gallione, 1981; Rose and Schubert, 1987 and Schubert et al., 1985; U.S. Pat. Nos. 6,033,886; 6,168,943).

VSV is an arthropod borne virus that can be transmitted to a variety of mammalian hosts, most commonly cattle, horses, swine and rodents. VSV infection of humans is uncommon, and in general is either asymptomatic or characterized by mild flu-like symptoms that resolve in three to eight days without complications. Because VSV is not considered a human pathogen, and pre-existing immunity to VSV is rare in the human population, the development of VSV derived vectors has been a focus in areas such as immunogenic compositions and gene therapy. For example, studies have established that VSV can serve as a highly effective vector for immunogenic compositions, expressing influenza virus haemagglutinin (Roberts et al., 1999), measles virus H protein (Schlereth et al., 2000) and HIV-1 env and gag proteins (Rose et al., 2001). Other characteristics of VSV that render it an attractive vector include: (a) the ability to replicate robustly in cell culture; (b) the inability to either integrate into host cell DNA or undergo genetic recombination; (c) the existence of multiple serotypes, allowing the possibility for prime-boost immunization strategies; (d) foreign genes of interest can be inserted into the VSV genome and expressed abundantly by the viral transcriptase; and (e) the development of a highly specialized system for the rescue of infectious virus from a cDNA copy of the virus genome (U.S. Pat. Nos. 6,033,886; 6,168,943).

Although there is little evidence of VSV neurological involvement during natural infection, animals (e.g., primates, rodents, herd animals) that are inoculated intracerebrally (and in the case of rodents intranasally) with wild-type virus, mouse brain passaged wild-type virus or cell culture adapted wild-type virus, can develop clinical signs of disease, and usually die two to eight days post inoculation. Because of these observations, and the need to produce a vector for immunogenic compositions for use in humans that has an exceptional safety profile, VSV vectors under development are tested in stringent, primate and small animal neurovirulence models. These tests are designed to detect any residual virulence in attenuated VSV vectors before consideration for advancement to human clinical trials.

The attenuation of prototypic-VSV vectors resulted from the accumulation of multiple nucleotide substitutions throughout the virus genome during serial passage in vitro and the synthesis and assembly of the genome cDNA. These mutations had pleiotropic effects that rendered the virus less pathogenic in mice than the lab-adapted virus from which it was derived (e.g., see Roberts et al., 1998). Prototypic further attenuated VSV vectors were also developed by truncation of the cytoplasmic tail region of the virus G protein, leading to VSV mutants that were defective in budding from the plasma membrane of infected cells (Schnell et al., 1998).

Currently known VSV vectors, putatively attenuated or not, have had unacceptable levels of residual virulence when tested in small animal and non-human primate neurovirulence models. The development of a VSV vector for uses such as a vector for immunogenic compositions, a gene therapy vector and the like, will require VSV vectors having minimal to non-detectable levels of pathogenicity in animal neurovirulence models. Thus, there is presently a need in the art of viral vectors to identify genetically modified, attenuated VSV mutants having significantly reduced (or eliminated) pathogenicity in mammals.

SUMMARY OF THE INVENTION

The present invention broadly relates to the synergistic attenuation of vesicular stomatitis virus (VSV). More particularly, the invention relates to the identification of combined mutation classes which synergistically attenuate the pathogenicity of VSV vectors in mammals and immunogenic compositions thereof.

Thus, in certain embodiments, the invention is directed to a genetically modified VSV comprising at least two different classes of mutations in its genome, wherein the two mutations synergistically attenuate VSV pathogenicity. In one particular embodiment, VSV pathogenicity is further defined as neurovirulence. In another embodiment, the classes of mutations are a temperature-sensitive (ts) mutation, a point mutation, a gene shuffling mutation, a G-stem mutation, a non-cytopathic M gene mutation, an ambisense RNA mutation, a truncated G gene mutation, a G gene insertion mutation and a gene deletion mutation.

In one particular embodiment, the two VSV mutations are a truncated G gene mutation (hereinafter, "$G_{(ct)}$") and a N gene shuffling mutation (that is, the N gene is moved away from its wild-type 3' promoter-proximal first position, to a more distal position in the gene order of VSV). In another embodiment, the VSV G protein encoded by the truncated G gene has a deletion in the last twenty carboxy-terminal amino acids (hereinafter, "$G_{(ct-9)}$"). In yet another embodiment, the VSV G protein encoded by the truncated G gene has a deletion of the last twenty-eight carboxy-terminal amino acids (hereinafter, "$G_{(ct-1)}$"). In still another embodiment, the VSV N gene is shuffled to 3'-PNMGL-5' or 3'-PMNGL-5', relative to the wild-type VSV genome 3'-NPMGL-5', wherein N is the gene encoding the nucleocapsid protein, P is the gene encoding the phosphoprotein, M is the gene encoding the matrix protein, G is the gene encoding the attachment glycoprotein and L is the gene encoding the RNA-dependent RNA polymerase protein. In certain embodiments, the VSV comprises a mutated genome of 3'-PNMG$_{(ct-1)}$L-5', 3'-PNMG$_{(ct-9)}$L-5', 3'-PMNG$_{(ct-1)}$L-5' or 3'-PMNG$_{(ct-9)}$L-5', wherein N is the gene encoding the nucleocapsid protein, P is the gene encoding the phosphoprotein, M is the gene encoding the matrix protein, $G_{(ct-1)}$ is the gene encoding the attachment glycoprotein having a cytoplasmic tail region consisting of one amino acid, $G_{(ct-9)}$ is the gene encoding the attachment glycoprotein having a cytoplasmic tail region consisting of nine amino acids and L is the gene encoding the RNA-dependent RNA polymerase protein. In one particular embodiment, the mutated VSV genome is 3'-PMNG$_{(ct-1)}$L-5'. In another particular embodiment, the mutated VSV genome is 3'-PNMG$_{(ct-1)}$L-5'. In another embodiment, the VSV further comprises a third class of mutation in its genome, wherein the mutation is a ts mutation, a point mutation, an ambisense RNA mutation, a G-stem mutation, a G gene insertion, a gene deletion or a non-cytopathic M gene mutation.

In certain embodiments, the modified VSV injected intracranially in 4-week old female Swiss-Webster mice has a $LD_{50}$ 100-fold greater than wild-type VSV injected intracranially in 4-week old female Swiss-Webster mice. In certain other embodiments, the VSV injected intracranially in 4-week old female Swiss-Webster mice has a $LD_{50}$ 1,000-fold greater than wild-type VSV injected intracranially in 4-week old female Swiss-Webster mice. In still other embodiments, the VSV injected intracranially in 4-week old female Swiss-Webster mice has a $LD_{50}$ 10,000-fold greater than wild-type VSV injected intracranially in 4-week old female Swiss-Webster mice. In yet other embodiments, the VSV injected intracranially in 4-week old female Swiss-Webster mice has a $LD_{50}$ 100,000-fold greater than wild-type VSV injected intracranially in 4-week old female Swiss-Webster mice.

In other embodiments of the invention, the two VSV mutations are a truncated G gene mutation and a non-cytopathic M gene mutation. In certain embodiments, the G protein encoded by the truncated G gene has a cytoplasmic tail domain consisting of one amino acid ($G_{(ct-1)}$) or a cytoplasmic tail domain consisting of nine amino acids ($G_{(ct-9)}$). In other embodiments, the M gene non-cytopathic mutation (hereinafter, "$M_{(ncp)}$") is a mutation of methionine to alanine at position 33 (M33A) and a mutation of methionine to alanine at position 51 (M51A) of the M protein. In one particular embodiment, the VSV comprises a mutated genome of 3'-NPM$_{(ncp)}$G$_{(ct-1)}$L-5' or 3'-NPM$_{(ncp)}$G$_{(ct-9)}$L-5'. In another embodiment, the VSV further comprises a third class of mutation in its genome, wherein the mutation is a ts mutation, an ambisense RNA mutation, a gene shuffling mutation, a gene deletion mutation, a gene insertion mutation, a G gene insertion mutation, a G-stem mutation or a point mutation.

As set forth below in Section A.3, a ts mutation of any one the VSV G, M, N, P or L genes is a separate "mutation class" of the invention. Thus, in certain embodiments of the invention, the two VSV mutations are a ts N gene mutation (hereinafter, "$N_{(ts)}$") and a ts L gene mutation (hereinafter, "$L_{(ts)}$"). In one particular embodiment, the VSV comprises a mutated genome of 3'-$N_{(ts)}$PMG$L_{(ts)}$-5'. In certain other embodiments, the VSV further comprises a third class of mutation in its genome, wherein the mutation is a point mutation, a gene shuffling mutation, a G-stem mutation, a non-cytopathic M gene mutation, an ambisense RNA mutation, a truncated G gene mutation, a G gene insertion mutation or a gene deletion mutation.

In certain embodiments, the two VSV mutations are a G-stem mutation (hereinafter, "$G_{(stem)}$") and a gene shuffling mutation. In other embodiments, the VSV further comprises a third class of mutation in its genome, wherein the mutation is a point mutation, a ts mutation, a gene shuffling mutation, a non-cytopathic M gene mutation, an ambisense RNA mutation, a truncated G gene mutation, a G gene insertion mutation and a gene deletion mutation.

In another embodiment, the invention is directed to a genetically modified VSV vector comprising at least two different classes of mutations in its genome and at least one foreign RNA sequence as a separate transcriptional unit inserted into or replacing a region of the VSV genome non-essential for replication, wherein the two mutations synergistically attenuate VSV pathogenicity. As defined hereinafter, a "foreign RNA" sequence is any polynucleotide sequence which is not endogenous to genome of wild-type VSV. In one particular embodiment, vector pathogenicity is further defined as neurovirulence. In certain other embodiments, the foreign RNA is defined as an open reading frame (ORF). In certain other embodiments, the classes of mutations are selected from the group consisting of a ts mutation, a point mutation, a gene shuffling mutation, a G-stem mutation, a non-cytopathic M gene mutation, an ambisense RNA mutation, a truncated G gene mutation, a G gene insertion mutation and a gene deletion mutation.

In one particular embodiment, the two VSV vector mutations are a truncated G gene mutation and a N gene shuffling mutation. In another embodiment, the G protein encoded by the truncated G gene has a deletion of the last twenty carboxy-terminal amino acids or a deletion of the last twenty-eight carboxy-terminal amino acids. In certain other embodiments, the N gene VSV vector is shuffled to 3'-PNMGL-5' or 3'-PMNGL-5', relative to the wild-type VSV genome 3'-NPMGL-5'. In one particular embodiment, the VSV vector comprises a mutated genome of 3'-PNMG$_{(ct-1)}$L-5', 3'-PNMG$_{(ct-9)}$L-5', 3'-PMNG$_{(ct-1)}$L-5' or 3'-PMNG$_{(ct-9)}$L-5'. In one particular embodiment, the mutated vector genome is 3'-PMNG$_{(ct-1)}$L-5'. In another embodiment, the mutated vector genome is 3'-PNMG$_{(ct-1)}$L-5'.

In yet other embodiments, the VSV vector further comprises a third class of mutation in its genome, wherein the mutation is a ts mutation, a point mutation, an ambisense RNA mutation, a G-stem mutation, a G gene insertion mutation, a gene deletion mutation or a non-cytopathic M gene mutation. In certain other embodiments, the VSV injected intracranially in 4-week old female Swiss-Webster mice has a $LD_{50}$ 100-fold greater than wild-type VSV injected intracranially in 4-week old female Swiss-Webster mice. In still other embodiments, the modified VSV injected intracranially in 4-week old female Swiss-Webster mice has a $LD_{50}$ 1,000-fold greater than wild-type VSV injected intracranially in 4-week old female Swiss-Webster mice. In yet other embodiments, the VSV injected intracranially in 4-week old female Swiss-Webster mice has a $LD_{50}$ 10,000-fold greater than wild-type VSV injected intracranially in 4-week old female Swiss-Webster mice. In another embodiment, the VSV injected intracranially in 4-week old female Swiss-Webster mice has a $LD_{50}$ 100,000-fold greater than wild-type VSV injected intracranially in 4-week old female Swiss-Webster mice.

In certain other embodiments, the foreign RNA inserted into or replacing a region of the VSV genome non-essential for replication is selected from the group consisting of a HIV gene, a HTLV gene, a SIV gene, a RSV gene, a PIV gene, a HSV gene, a CMV gene, an Epstein-Barr virus gene, a Varicella-Zoster virus gene, a mumps virus gene, a measles virus gene, an influenza virus gene, a poliovirus gene, a rhinovirus gene, a hepatitis A virus gene, a hepatitis B virus gene, a hepatitis C virus gene, a Norwalk virus gene, a togavirus gene, an alphavirus gene, a rubella virus gene, a rabies virus gene, a Marburg virus gene, an Ebola virus gene, a papilloma virus gene, a polyoma virus gene, a metapneumovirus gene, a coronavirus gene, a *Vibrio cholera* gene, a *Streptococcus pneumoniae* gene, *Streptococcus pyogenes* gene, a *Streptococcus agalactiae* gene, a *Neisseria meningitidis* gene, a *Neisseria gonorrheae* gene, a *Corynebacteria diphtheria* gene, a *Clostridium tetani* gene, a *Bordetella pertussis* gene, a *Helicobacter pylori* gene, a *Haemophilus* gene, a *Chlamydia* gene, a *Escherichia coli* gene, a cytokine gene, a T-helper epitope, a CTL epitope, an adjuvant gene and a co-factor gene. In one particular embodiment, the foreign RNA is a HIV gene selected from the group consisting of gag, env, pol, vif, nef, tat, vpr, rev and vpu. In one particular embodiment, the HIV gene is gag, wherein the gag gene is inserted into the VSV genome at position one or at position five. In particular embodiments, the genome of the mutated VSV vector is 3'-gag$_1$-PNMG$_{(ct-1)}$L-5', 3'-gag$_1$-PNMG$_{(ct-9)}$L-5', 3'-gag$_1$-PMNG$_{(ct-1)}$L-5', 3'-gag$_1$-PMNG$_{(ct-9)}$L-5', 3'-PNMG$_{(ct-1)}$L-gag$_5$-5', 3'-PNMG$_{(ct-9)}$L-gag$_5$-5', 3'-PMNG$_{(ct-1)}$ L-gag$_5$-5' or 3'-PMNG$_{(ct-9)}$L-gag$_5$-5'.

In another embodiment, the foreign RNA expresses a tumor specific antigen or tumor-associated antigen, for induction of a protective immune response against a tumor (e.g., a malignant tumor). Such tumor-specific or tumor-associated antigens include, but are not limited to, KS 1/4 pan-carcinoma antigen; ovarian carcinoma antigen (CA125); prostatic acid phosphate; prostate specific antigen; melanoma-associated antigen p97; melanoma antigen gp75; high molecular weight melanoma antigen and prostate specific membrane antigen.

In certain other embodiments, the two VSV vector mutations are a G$_{(ct)}$ mutation and a M$_{(ncp)}$ mutation. In certain embodiments, the G protein encoded by the truncated G gene has a cytoplasmic tail domain consisting of one amino acid (G$_{(ct-1)}$) or a cytoplasmic tail domain consisting of nine amino acids (G$_{(ct-9)}$). In yet other embodiments, the M$_{(ncp)}$ mutation is a mutation of methionine to alanine at position 33 (M33A) and a mutation of methionine to alanine at position 51 (M51A) of the M protein. In one particular embodiment, the mutated genome is 3'-NPM$_{(ncp)}$G$_{(ct-1)}$ L-5' or 3'-NPM$_{(ncp)}$G$_{(ct-9)}$L-5'. In another embodiment, the vector further comprises a third class of mutation in its genome, wherein the mutation is a ts mutation, a point mutation, a gene shuffling mutation, a G-stem mutation, an ambisense RNA mutation, a G gene insertion mutation and a gene deletion mutation. In certain embodiments, the VSV vector comprises an HIV gene selected from the group consisting of gag, env, pol, vif, nef, tat, vpr, rev or vpu. In one particular embodiment, the HIV gene is gag, wherein the mutated genome is 3'-gag$_1$-NPM$_{(ncp)}$G$_{(ct-1)}$L-5', 3'-gag$_1$-NPM$_{(ncp)}$G$_{(ct-9)}$L-5', 3'-NPM$_{(ncp)}$G$_{(ct-1)}$L-gag$_5$-5' or 3'-NPM$_{(ncp)}$G$_{(ct-9)}$L-gag$_5$-5'.

In still other embodiments, the two VSV vector mutations are a N$_{(ts)}$ gene mutation and a L$_{(ts)}$ gene mutation. In one particular embodiment, the vector comprises a mutated genome of 3'-N$_{(ts)}$PMGL$_{(ts)}$-5'. In other embodiments, the vector further comprises a third class of mutation in its genome, wherein the mutation is a point mutation, a gene shuffling mutation, a G-stem mutation, a non-cytopathic M gene mutation, an ambisense RNA mutation, a truncated G gene mutation, a G gene insertion mutation and a gene deletion mutation. In certain embodiments, the VSV vector comprises an HIV gene selected from the group consisting of gag, env, pol, vif, nef, tat, vpr, rev or vpu. In one particular embodiment, the HIV gene is gag, wherein the mutated genome is 3'-gag$_1$-N$_{(ts)}$PMGL$_{(ts)}$-5' or 3'-N$_{(ts)}$PMGL$_{(ts)}$-gag$_5$-5'.

As set forth below in Section A.1, the insertion of a foreign nucleic acid sequence (e.g., HIV gag) into the VSV genome 3' to any of the N, P, M, G or L genes effectively results in a "gene shuffling mutation". Thus, in certain embodiments, the two VSV vector mutations are G$_{(stem)}$ mutation and a gene shuffling mutation. In one embodiment, the mutated vector genome is 3'-gag$_1$-NPMG$_{(stem)}$L-5'. In other embodiments, the VSV vector further comprises a third class of mutation in its genome, wherein the mutation is a point mutation, a ts mutation, a gene shuffling mutation, a non-cytopathic M gene mutation, an ambisense RNA mutation, a truncated G gene mutation, a G gene insertion mutation and a gene deletion mutation.

In another embodiment, the invention is directed to an immunogenic composition comprising an immunogenic dose of a genetically modified VSV vector comprising at least two different classes of mutations in its genome and at least one foreign RNA sequence as a separate transcriptional unit inserted into or replacing a region of the VSV genome non-essential for replication, wherein the two mutations synergistically attenuate VSV pathogenicity. In another embodiment, the classes of mutations are selected from the group consisting of a ts mutation, a point mutation, a gene shuffling mutation, a G-stem mutation, a non-cytopathic M gene mutation, an ambisense RNA mutation, a truncated G gene mutation, a G gene insertion mutation and a gene deletion mutation.

In certain embodiments, the two mutations are a truncated G gene mutation and a N gene shuffling mutation. In particular embodiments, the G protein encoded by the truncated G gene has a cytoplasmic tail domain consisting of one amino acid (G$_{(ct-1)}$) or a cytoplasmic tail domain consisting of nine amino acids (G$_{(ct-9)}$). In still other embodiments, the N gene is shuffled to 3'-PNMGL-5' or 3'-PMNGL-5', relative to the wild-type VSV genome 3'-NPMGL-5'. In certain embodiments, the VSV vector of the immunogenic composition comprises a mutated genome of 3'-PNMG$_{(ct-1)}$L-5', 3'-PNMG$_{(ct-9)}$L-5', 3'-PMNG$_{(ct-1)}$L-5' or 3'-PMNG$_{(ct-9)}$ L-5'. In one particular embodiment, the mutated vector genome of the immunogenic composition is 3'-PMNG$_{(ct-1)}$L-5'. In another embodiment, the mutated vector genome is 3'-PNMG$_{(ct-1)}$L-5'. In other embodiments, the VSV vector of the immunogenic composition further comprises a third class of mutation in its genome, wherein the mutation is a ts mutation, an ambisense RNA mutation, a point mutation, a G-stem mutation, a G gene insertion mutation, a gene deletion mutant or a non-cytopathic M gene mutation.

In certain other embodiments, the foreign RNA inserted into the genetically modified VSV vector of the immunogenic composition is selected from the group consisting of a HIV gene, a HTLV gene, a SIV gene, a RSV gene, a PIV gene, a HSV gene, a CMV gene, an Epstein-Barr virus gene, a Varicella-Zoster virus gene, a mumps virus gene, a measles virus gene, an influenza virus gene, a poliovirus gene, a rhinovirus gene, a hepatitis A virus gene, a hepatitis B virus gene, a hepatitis C virus gene, a Norwalk virus gene, a togavirus gene, an alphavirus gene, a rubella virus gene, a rabies virus gene, a Marburg virus gene, an Ebola virus gene, a papilloma virus gene, a polyoma virus gene, a metapneumovirus gene, a coronavirus gene, a *Vibrio cholera* gene, a *Streptococcus pneumoniae* gene, *Streptococcus pyogenes* gene, a *Streptococcus agalactiae* gene, a *Neisseria meningitidis* gene, a *Neisseria gonorrheae* gene, a *Corynebacteria diphtheria* gene, a *Clostridium tetani* gene, a *Bordetella pertussis* gene, a *Helicobacter pylori* gene, a *Haemophilus* gene, a *Chlamydia* gene, a *Escherichia coli* gene, a cytokine gene, a T-helper epitope, a CTL epitope, an adjuvant gene and a co-factor gene. In one particular embodiment, the foreign RNA encodes a HIV protein selected from the group consisting of gag, env, pol, vif, nef, tat, vpr, rev and vpu. In one particular embodiment, the HIV gene is gag, wherein the gag gene is inserted into the VSV genome at position one or at position five of the genome. In another embodiment, the VSV vector of the immunogenic composition comprises a mutated genome of 3'-gag$_1$-PNMG$_{(ct-1)}$L-5', 3'-gag$_1$-PNMG$_{(ct-9)}$L-5', 3'-gag$_1$-PMNG$_{(ct-1)}$L-5', 3'-gag$_1$-PMNG$_{(ct-9)}$L-5', 3'-PNMG$_{(ct-1)}$L-gag$_5$-5', 3'-PNMG$_{(ct-9)}$L-gag$_5$-5', 3'-PMNG$_{(ct-1)}$L-gag$_5$-5' or 3'-PMNG$_{(ct-9)}$L-gag$_5$-5'.

In certain other embodiments, the VSV vector of the immunogenic composition comprises a G$_{(ct)}$ mutation and a M$_{(ncp)}$ mutation. In another embodiment, the G protein encoded by the truncated G gene has a cytoplasmic tail domain consisting of one amino acid (G$_{(ct-1)}$) or a cytoplasmic tail domain consisting of nine amino acids (G$_{(ct-9)}$). In another embodiment, the M$_{(ncp)}$ mutation is a mutation of methionine to alanine at position 33 (M33A) and a mutation of methionine to alanine at position 51 (M51A) of the M protein. In one particular embodiment, the immunogenic composition comprises a mutated VSV genome of 3'-NPM$_{(ncp)}$G$_{(ct-1)}$L-5' or 3'-NPM$_{(ncp)}$G$_{(ct-9)}$L-5'. In yet other embodiments, the VSV vector of the immunogenic composition further comprises a third class of mutation in its genome, wherein the mutation is a ts mutation, a point mutation, a gene shuffling mutation, a G-stem mutation, an ambisense RNA mutation, a G gene insertion mutation and a gene deletion mutation. In yet other embodiments, the foreign RNA inserted into the genetically modified VSV vector of the immunogenic composition is selected from the group consisting of a HIV gene, a HTLV gene, a SIV gene, a RSV gene, a PIV gene, a HSV gene, a CMV gene, an Epstein-Barr virus gene, a Varicella-Zoster virus gene, a mumps virus gene, a measles virus gene, an influenza virus gene, a poliovirus gene, a rhinovirus gene, a hepatitis A virus gene, a hepatitis B virus gene, a hepatitis C virus gene, a Norwalk virus gene, a togavirus gene, an alphavirus gene, a rubella virus gene, a rabies virus gene, a Marburg virus gene, an Ebola virus gene, a papilloma virus gene, a polyoma virus gene, a metapneumovirus gene, a coronavirus gene, a *Vibrio cholerae* gene, a *Streptococcus pneumoniae* gene, *Streptococcus pyogenes* gene, a *Helicobacter pylori* gene, a *Streptococcus agalactiae* gene, a *Neisseria meningitidis* gene, a *Neisseria gonorrheae* gene, a *Corynebacteria diphtheriae* gene, a *Clostridium tetani* gene, a *Bordetella pertussis* gene, a *Haemophilus* gene, a *Chlamydia* gene, a *Escherichia coli* gene, a gene encoding a cytokine, a gene encoding T-helper epitope, a gene encoding a CTL epitope, a gene encoding an adjuvant and a gene encoding a co-factor. In certain embodiments, the HIV gene is selected from the group consisting of gag, env, pol, vif, net, tat, vpr, rev or vpu. In one particular embodiment, the HIV gene is gag, wherein the mutated genome is 3'-gag$_1$-NPM$_{(ncp)}$G$_{(ct-1)}$L-5', 3'-gag$_1$-NPM$_{(ncp)}$G$_{(ct-9)}$L-5', 3'-NPM$_{(ncp)}$G$_{(ct-1)}$L-gag$_5$-5' or 3'-NPM$_{(ncp)}$G$_{(ct-9)}$L-gag$_5$-5'.

In certain other embodiments, the immunogenic composition comprises a N$_{(ts)}$ gene mutation and a L$_{(ts)}$ gene mutation. In one particular embodiment, the immunogenic composition comprises a mutated VSV genome of 3'-N$_{(ts)}$PMGL$_{(ts)}$-5'. In other embodiments, the immunogenic composition further comprises a third class of mutation in its genome, wherein the mutation is a point mutation, a gene shuffling mutation, a G-stem mutation, a non-cytopathic M gene mutation, an ambisense RNA mutation, a truncated G gene mutation, a G gene insertion mutation and a gene deletion mutation. In yet other embodiments, the foreign RNA inserted into the genetically modified VSV vector of the immunogenic composition is selected from the group consisting of a HIV gene, a HTLV gene, a SIV gene, a RSV gene, a PIV gene, a HSV gene, a CMV gene, an Epstein-Barr virus gene, a Varicella-Zoster virus gene, a mumps virus gene, a measles virus gene, an influenza virus gene, a poliovirus gene, a rhinovirus gene, a hepatitis A virus gene, a hepatitis B virus gene, a hepatitis C virus gene, a Norwalk virus gene, a togavirus gene, an alphavirus gene, a rubella virus gene, a rabies virus gene, a Marburg virus gene, an Ebola virus gene, a papilloma virus gene, a polyoma virus gene, a metapneumovirus gene, a coronavirus gene, a *Vibrio cholerae* gene, a *Streptococcus pneumoniae* gene, *Streptococcus pyogenes* gene, a *Helicobacter pylori* gene, a *Streptococcus agalactiae* gene, a *Neisseria meningitidis* gene, a *Neisseria gonorrheae* gene, a *Corynebacteria diphtheriae* gene, a *Clostridium tetani* gene, a *Bordetella pertussis* gene, a *Haemophilus* gene, a *Chlamydia* gene, a *Escherichia coli* gene, a gene encoding a cytokine, a gene encoding T-helper epitope, a gene encoding a CTL epitope, a gene encoding an adjuvant and a gene encoding a co-factor. In certain embodiments, the HIV gene is selected from the group consisting of gag, env, pol, vif, net, tat, vpr, rev or vpu. In one particular embodiment, the HIV gene is gag, wherein the mutated genome is 3'-gag$_1$-N$_{(ts)}$PMGL$_{(ts)}$-5' or 3'-N$_{(ts)}$PMGL$_{(ts)}$-gag$_5$-5'.

In certain other embodiments, the immunogenic composition comprises a G$_{(stem)}$ mutation and a gene shuffling mutation. In one particular embodiment, the immunogenic composition comprises a mutated genome of 3'-gag$_1$-NPMG$_{(stem)}$L-5'. In other embodiments, the immunogenic composition further comprises a third class of mutation in its genome, wherein the mutation is a point mutation, a ts mutation, a gene shuffling mutation, a non-cytopathic M gene mutation, an ambisense RNA mutation, a truncated G gene mutation, a G gene insertion mutation and a gene deletion mutation.

In still another embodiment, an immunogenic composition of the invention is administered by any conventional route selected from the group consisting of intravenous, intradermal, subcutaneous, intramuscular, intraperitoneal, oral, rectal, intranasal, buccal, vaginal and ex vivo.

In another embodiment, the invention is directed to a method of immunizing a mammalian subject against HIV infection comprising administering to the subject an immunogenic dose of a genetically modified VSV vector comprising at least two different classes of mutations in its genome and at least one HIV RNA sequence as a separate transcriptional unit inserted into or replacing a region of the VSV genome non-essential for replication, wherein the two mutations synergistically attenuate VSV pathogenicity and the HIV RNA encodes an antigen selected from the group consisting gag, env, pol, vif, nef, tat, vpr, rev and vpu. In certain embodiments, the VSV vector is 3'-gag$_1$-PNMG$_{(ct-1)}$L-5', 3'-gag$_1$-PNMG$_{(ct-9)}$L-5', 3'-gag$_1$-PMNG$_{(ct-1)}$L-5', 3'-gag$_1$-PMNG$_{(ct-9)}$L-5', 3'-PNMG$_{(ct-1)}$L-gag$_5$-5', 3'-PNMG$_{(ct-9)}$L-gag$_5$-5', 3'-PMNG$_{(ct-1)}$L-gag$_5$-5', 3'-PMNG$_{(ct-9)}$L-gag$_5$-5', 3'-gag$_1$-NPM$_{(ncp)}$G$_{(ct-1)}$L-5', 3'-gag$_1$-NPM$_{(ncp)}$G$_{(ct-9)}$L-5', 3'-NPM$_{(ncp)}$G$_{(ct-1)}$L-gag$_5$-5', 3'-NPM$_{(ncp)}$G$_{(ct-9)}$L-gag$_5$-5', 3'-gag$_1$-N$_{(ts)}$PMGL$_{(ts)}$-5' or 3'-N$_{(ts)}$PMGL$_{(ts)}$-gag$_5$-5'.

In certain other embodiments, the invention is directed to a method of immunizing a mammalian host against bacterial infection comprising administering an immunogenic dose of a genetically modified VSV vector comprising (a) at least two different classes of mutations in its genome, the mutations selected from the group consisting of a ts mutation, a point mutation, a gene shuffling mutation, a G-stem mutation, a non-cytopathic M gene mutation, an ambisense RNA mutation, a truncated G gene mutation, a G gene insertion mutation and a gene deletion mutation, wherein the two mutations synergistically attenuate VSV pathogenicity and (b) at least one foreign RNA sequence inserted into or replacing a region of the VSV genome non-essential for replication, wherein the RNA encodes a bacterial protein selected from the group consisting of a *Vibrio cholerae* protein, a *Streptococcus pneu-* moniae protein, Streptococcus pyogenes protein, a Streptococcus agalactiae protein, a Helicobacter pylori protein, a Neisseria meningitidis protein, a Neisseria gonorrheae protein, a Corynebacteria diphtheriae protein, a Clostridium tetani protein, a Bordetella pertussis protein, a Haemophilus protein, a Chlamydia protein and a Escherichia coli protein.

In one particular embodiment, the two mutations are a $G_{(ct)}$ mutation and a N gene shuffling mutation. In certain embodiments, the G protein encoded by the truncated G gene has a cytoplasmic tail domain consisting of one amino acid ($G_{(ct-1)}$) or a cytoplasmic tail domain consisting of nine amino acids $G_{(ct-9)}$. In certain other embodiments, the N gene is shuffled to 3'-PNMGL-5' or 3'-PMNGL-5', relative to the wild-type VSV genome 3'-NPMGL-5'. In other embodiments, the mutated VSV genome is 3'-PNMG$_{(ct-1)}$L-5', 3'-PNMG$_{(ct-9)}$L-5', 3'-PMNG$_{(ct-1)}$L-5' or 3'-PMNG$_{(ct-9)}$L-5'. In one particular embodiment, the mutated genome is 3'-PMNG$_{(ct-1)}$L-5' or 3'-PNMG$_{(ct-1)}$L-5'.

In other embodiments, the VSV further comprises a third class of mutation in its genome, wherein the mutation is a ts mutation, a point mutation, an ambisense RNA mutation, a gene deletion mutation, a G-stem mutation, a G gene insertion mutation, a gene insertion mutation or a non-cytopathic M gene mutation.

In another embodiment, the invention is directed to a method of immunizing a mammalian host against viral infection comprising administering an immunogenic dose of a genetically modified VSV vector comprising (a) at least two different classes of mutations in its genome, the mutations selected from the group consisting of a ts mutation, a point mutation, a gene shuffling mutation, a G-stem mutation, a non-cytopathic M gene mutation, an ambisense RNA mutation, a truncated G gene mutation, a G gene insertion mutation and a gene deletion mutation, wherein the two mutations synergistically attenuate VSV pathogenicity and (b) at least one foreign RNA sequence inserted into or replacing a region of the VSV genome non-essential for replication, wherein the RNA encodes a viral protein selected from the group consisting of a HIV protein, a HTLV protein, a SIV protein, a RSV protein, a PIV protein, a HSV protein, a CMV protein, an Epstein-Barr virus protein, a Varicella-Zoster virus protein, a mumps virus protein, a measles virus protein, an influenza virus protein, a poliovirus protein, a rhinovirus protein, a hepatitis A virus protein, a hepatitis B virus protein, a hepatitis C virus protein, a Norwalk virus protein, a togavirus protein, an alphavirus protein, a rubella virus protein, a rabies virus protein, a Marburg virus protein, an Ebola virus protein, a papilloma virus protein, a polyoma virus protein, a metapneumovirus protein and a coronavirus protein. In one particular embodiment, the RNA is a HIV gene selected from the group consisting of gag, env, pol, vif, nef, tat, vpr, rev or vpu.

In certain embodiments, the two mutations are a $G_{(ct)}$ mutation and a N gene shuffling mutation. In one particular embodiment, the mutated VSV genome is 3'-PNMG$_{(ct-1)}$L-5', 3'-PNMG$_{(ct-9)}$L-5', 3'-PMNG$_{(ct-1)}$L-5' or 3'-PMNG$_{(ct-9)}$L-5'. In another embodiment, the HIV gene is gag, wherein the gag gene is inserted into the VSV genome at position one or at position five, wherein the mutated genome is 3'-gag$_1$-PNMG$_{(ct-1)}$L-5', 3'-gag$_1$-PNMG$_{(ct-9)}$L-5', 3'-gag$_1$-PMNG$_{(ct-1)}$L-5', 3'-gag$_1$-PMNG$_{(ct-9)}$L-5', 3'-PNMG$_{(ct-1)}$L-gag$_5$-5', 3'-PNMG$_{(ct-9)}$L-gag$_5$-5', 3'-PMNG$_{(ct-1)}$L-gag$_5$-5' or 3'-PMNG$_{(ct-9)}$L-gag$_5$-5'. In another embodiment, the VSV further comprises a third class of mutation in its genome, wherein the mutation is a ts mutation, a point mutation, an ambisense RNA mutation, a gene deletion mutation, a G-stem mutation, s G gene insertion mutation, a gene insertion mutation or a non-cytopathic M gene mutation.

In other embodiments of the method of immunizing a mammalian host against viral infection, the two VSV mutations are a $G_{(ct)}$ mutation and $M_{(ncp)}$ mutation. In one particular embodiment, the mutated VSV genome is 3'-NPM$_{(ncp)}$ G$_{(ct-1)}$L-5' or 3'-NPM$_{(ncp)}$G$_{(ct-9)}$L-5'. In another embodiment, the mutated VSV genome is 3'-gag$_1$-NPM$_{(ncp)}$G$_{(ct-1)}$L-5', 3'-gag$_1$-NPM$_{(ncp)}$G$_{(ct-9)}$L-5', 3'-NPM$_{(ncp)}$G$_{(ct-1)}$L-gag$_5$-5' or 3'-NPM$_{(ncp)}$ G$_{(ct-9)}$L-gag$_5$-5'. In another embodiment, the VSV genome further comprises a third class of mutation in its genome, wherein the mutation is a ts mutation, a point mutation, a gene shuffling mutation, a G-stem mutation, an ambisense RNA mutation, a G gene insertion mutation and a gene deletion mutation.

In other embodiments of the method of immunizing a mammalian host against viral infection, the two VSV mutations are a $N_{(ts)}$ gene mutation and a $L_{(ts)}$ gene mutation. In one particular embodiment, the mutated VSV genome is 3'-N$_{(ts)}$PMGL$_{(ts)}$-5', 3'-gag$_1$-N$_{(ts)}$PMGL$_{(ts)}$-5' or 3'-N$_{(ts)}$ PMGL$_{(ts)}$-gag$_5$-5'. In another embodiment, the VSV genome further comprises a third class of mutation in its genome, wherein the mutation is a point mutation, a gene shuffling mutation, a G-stem mutation, a non-cytopathic M gene mutation, an ambisense RNA mutation, a truncated G gene mutation, a G gene insertion mutation and a gene deletion mutation.

In other embodiments of the method of immunizing a mammalian host against viral infection, the two VSV mutations are a are $G_{(stem)}$ mutation and a gene shuffling mutation. In one embodiment, the mutated genome is 3'-gag$_1$-NPMG$_{(stem)}$L-5'. In another embodiment, the VSV genome further comprises a third class of mutation in its genome, wherein the mutation is a point mutation, a ts mutation, a gene shuffling mutation, a non-cytopathic M gene mutation, an ambisense RNA mutation, a truncated G gene mutation, a G gene insertion mutation and a gene deletion mutation.

Other features and advantages of the invention will be apparent from the following detailed description, from the preferred embodiments thereof, and from the claims.

BRIEF DESCRIPTION OF THE FIGURES

FIG. 2 is a comparison of the growth kinetics of N shuffled VSV mutants (3'-PNMGL-5', 3'-PMNGL-5' and 3'-PMGNL-5') relative to wild-type VSV (3'-NPMGL-5') and G protein ct-1 VSV mutant (3'-NPMG$_{(ct-9)}$L-gag$_5$-5').

FIG. 3 shows a comparison of the growth rates of combined VSV N shuffled/G protein ct-1 mutants (3'-PNMG$_{(ct-1)}$L-5' and 3'-PMNG$_{(ct-1)}$L-5') relative to wild-type VSV (3'-NPMGL-5') and a G protein ct-1 VSV mutant (3'-NPMG$_{(ct-1)}$L-gag$_5$-5').

DETAILED DESCRIPTION OF THE INVENTION

Figure 1:
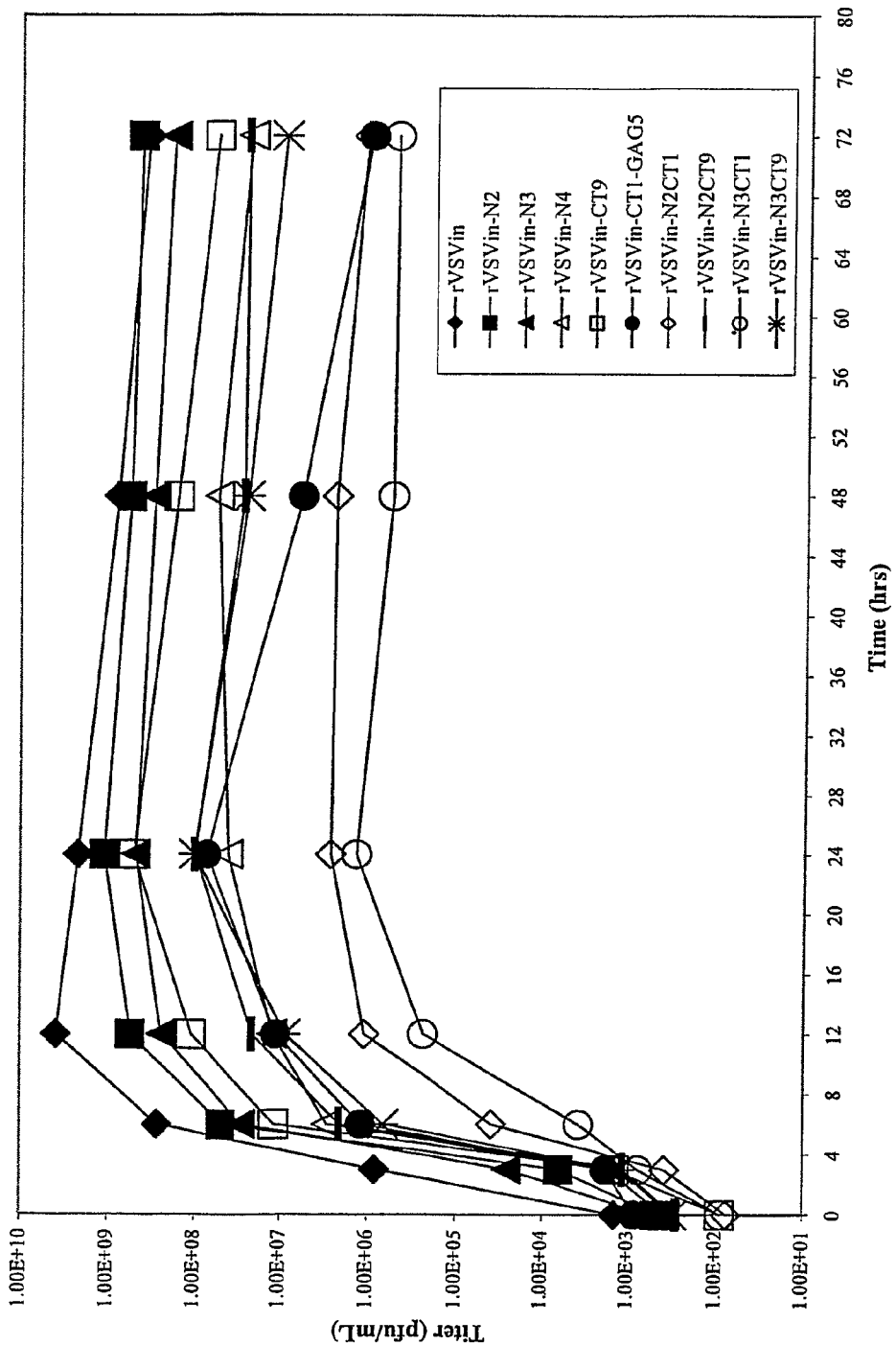
FIG. 1 shows the growth kinetics (pfu/mL versus time) of wild-type VSV (3'-NPMGL-5'), N shuffled VSV mutants (3'-PNMGL-5' [N2], 3'-PMNGL-5' [N3] and 3'-PMGNL-5' [N4]), G protein cytoplasmic tail (ct) truncation VSV mutants (3'-NPMG$_{(ct-9)}$ L-5' [CT9] and 3'-NPMG$_{(ct-1)}$L-gag$_5$-5' [CT1-GAG5]) and combined VSV N shuffled/G protein ct truncation mutants (3'-PNMG$_{(ct-1)}$L-5[N2CT1], 3'-PNMG$_{(ct-9)}$L-5' [N2CT9], 3'-PMNG$_{(ct-1)}$L-5' [N3CT1] and 3'-PMNG$_{(ct-9)}$L-5'[N3CT9]). The abbreviation "in" shown in the inset figure legend represents the Indiana strain of VSV.

The invention described hereinafter addresses a need in the art for vesicular stomatitis virus (VSV) vectors having significantly attenuated pathogenicity in mammals, particularly attenuated neuropathogenicity as revealed in animal neurovirulence models. As described above, VSV has many characteristics which make it an appealing vector for immunogenic compositions and/or gene therapy. For example, VSV infection of humans is uncommon and is either asymptomatic or characterized by mild flu-like symptoms that resolve in three to eight days without complications, and as such, VSV is not considered a human pathogen. Other characteristics of VSV that render it an attractive vector include: (a) the ability to replicate robustly in cell culture; (b) the inability to either integrate into host cell DNA or undergo genetic recombination; (c) the existence of multiple serotypes, allowing the possibility for prime-boost immunization strategies; (d) foreign genes of interest can be inserted into the VSV genome and expressed abundantly by the viral transcriptase; (e) the development of a highly specialized system for the rescue of infectious virus from a cDNA copy of the virus genome (U.S. Pat. Nos. 6,033,886; 6,168,943) and (f) pre-existing immunity to VSV in the human population is infrequent.

An early class of attenuated VSV vectors described in the art were referred to as temperature-sensitive (ts) mutants, wherein the ts mutants failed to produce virions at a restrictive temperature. For example, various VSV ts mutants are known in the art (e.g., see Holloway et al., 1970; Pringle et al., 1971; Evans et al., 1979; Pringle et al., 1981; Morita et al., 1987; Gopalakrishna and Lenard, 1985). In addition, further classes of attenuated VSV mutants have also been described in the art and include VSV G protein truncated cytoplasmic tail (ct) mutations (Schnell et al., 1998), gene shuffling (or gene order rearrangement) mutations (Wertz et al., 1998; Ball et al., 1999; Flanagan et al., 2001; U.S. Pat. No. 6,596,529), G-stem mutations (Jeetendra et al., 2003; Jeetendra et al., 2002; Robinson and Whitt, 2000), non-cytopathic M protein mutations (Jayakar et al., 2000; Jayakar and Whitt, 2002) and ambisense RNA mutations (Finke and Conzelmann, 1997; Finke and Conzelmann 1999). However, as stated above, currently available attenuated VSV vectors retain residual virulence when tested in animal models, and as such, are not likely vector candidates for advancement to human clinical trials.

As set forth in detail herein, the present invention relates to the unexpected and surprising observations that combinations of two or more known attenuating mutation classes (gene shuffling mutations, G protein insertion and truncation mutations, ts mutations and other point mutations, non-cytopathic M gene mutations, G-stem mutations, ambisense RNA mutations, gene deletion mutations, and the like) have a synergistic effect (in contrast to an additive effect) on the resulting level of attenuation of pathogenicity achieved. For example, it is demonstrated herein, that VSV G protein truncation mutants, when combined with shuffled N gene mutants, exerted a synergistic attenuation of VSV growth (Example 2) and neurovirulence (Example 3). In addition, certain embodiments of the present invention are directed to combinations of other classes of mutation, which also have a synergistic effect on VSV attenuation. Such classes include, but are not limited to: ts mutations, point mutations, gene shuffling mutations (including N, P, M, G and L gene shuffles), G-stem mutations, G gene insertions, non-cytopathic M gene mutations, truncated G gene mutations (e.g., a ct mutant), ambisense RNA mutations and gene deletion mutations.

Thus, in certain embodiments, the invention is directed to a genetically modified VSV vector comprising at least two different classes of mutations in its genome and at least one foreign RNA sequence as a separate transcriptional unit inserted into or replacing a region of the VSV genome non-essential for replication, wherein the two mutations synergistically attenuate VSV pathogenicity. In certain other embodiments, the invention is directed to immunogenic compositions comprising a genetically modified VSV vector comprising at least two different classes of mutations in its genome and at least one foreign RNA sequence as a separate transcriptional unit inserted into or replacing a region of the VSV genome non-essential for replication, wherein the two mutations synergistically attenuate VSV pathogenicity.

A. Vesicular Stomatitis Virus Mutation Classes

As stated above, a genetically modified VSV vector of the invention comprises at least two different classes of mutations in its genome. As defined hereinafter, the terms "mutation class", "mutation classes" or "classes of mutation" are used interchangeably, and refer to mutations known in the art, when used singly, to attenuate VSV. For example, a "mutation class" of the invention includes, but is not limited to, a VSV temperature-sensitive N gene mutation (hereinafter, "$N_{(ts)}$"), a temperature-sensitive L gene mutation (hereinafter, "$L_{(ts)}$"), a point mutation, a G-stem mutation (hereinafter, "$G_{(stem)}$"), a non-cytopathic M gene mutation (hereinafter, "$M_{(ncp)}$"), a gene shuffling or rearrangement mutation, a truncated G gene mutation (hereinafter, "$G_{(ct)}$"), an ambisense RNA mutation, a G gene insertion mutation, a gene deletion mutation and the like. As defined hereinafter, a "mutation" includes mutations known in the art as insertions, deletions, substitutions, gene rearrangement or shuffling modifications.

As defined hereinafter, the term "synergistic" attenuation refers to a level of VSV attenuation which is greater than additive. For example, a synergistic attenuation of VSV according to the present invention comprises combining at least two classes of mutation in the same VSV genome, thereby resulting in a reduction of VSV pathogenicity much greater than an additive attenuation level observed for each VSV mutation class alone. Thus, in certain embodiments, a synergistic attenuation of VSV is defined as a $LD_{50}$ at least greater than the additive attenuation level observed for each mutation class alone (i.e., the sum of the two mutation classes), wherein attenuation levels (i.e., the $LD_{50}$) are determined in a small animal neurovirulence model.

By way of a non-limiting example, if equation (1) describes an "additive attenuation" of VSV:

$$\Delta a_{LD50} + \Delta b_{LD50} = X_{LD50}; \quad (1)$$

wherein $\Delta a_{LD50}$ is the $LD_{50}$ of a VSV having a first mutation class in its genome, $\Delta b_{LD50}$ is the $LD_{50}$ of a VSV having a second mutation class in its genome and $X_{LD50}$ is the sum of $\Delta a_{LD50}$ and $\Delta b_{LD50}$; then a VSV "synergistic attenuation" of the invention, having a $LD_{50}$ at least greater than the additive attenuation level observed for each mutation class alone, is described by equation (2):

$$\Delta a,b_{LD50} > (\Delta a_{LD50} + \Delta b_{LD50}); \quad (2)$$

wherein $\Delta a,b_{LD50}$ is the $LD_{50}$ of a VSV having a combination of two mutation classes in its genome, $\Delta a_{LD50}$ is the $LD_{50}$ of a VSV having a first mutation class in its genome and $\Delta b_{LD50}$ is the $LD_{50}$ of a VSV having a second mutation class in its genome. Thus, in certain embodiments, the synergy of VSV attenuation (i.e., two mutation classes in the same VSV genome) is described relative to the $LD_{50}$ of two VSV constructs (each VSV construct having a single mutation class in its genome), wherein the synergistic attenuation of the VSV having two mutation classes in its genome is defined as a $LD_{50}$ at least greater than the additive $LD_{50}$ of the two VSV constructs having a single mutation class in their genome (e.g., see VSV $LD_{50}$ values in Table 7).

In certain other embodiments, the synergy of VSV attenuation is described relative to the $LD_{50}$ of a wild-type VSV. Thus, in one embodiment, a synergistic attenuation of VSV is defined as a $LD_{50}$ that is at least greater than the $LD_{50}$ of wild-type VSV, wherein the $LD_{50}$ is determined in an animal neurovirulence model. In one embodiment, a synergistic attenuation of VSV is defined as a $LD_{50}$ that is at least 10-fold greater than the $LD_{50}$ of wild-type VSV, wherein the $LD_{50}$ is determined in an animal neurovirulence model. In another embodiment, a synergistic attenuation of VSV is defined as a $LD_{50}$ that is at least 100-fold greater than the $LD_{50}$ of wild-type VSV, wherein the $LD_{50}$ is determined in an animal neurovirulence model. In another embodiment, a synergistic attenuation of VSV is defined as a $LD_{50}$ that is at least 1,000-fold greater than the $LD_{50}$ of wild-type VSV, wherein the $LD_{50}$ is determined in an animal neurovirulence model. In yet other embodiments, a synergistic attenuation of VSV is defined as a $LD_{50}$ that is at least 10,000-fold greater than the $LD_{50}$ of wild-type VSV, wherein the $LD_{50}$ is determined in an animal neurovirulence model. In certain other embodiments, a synergistic attenuation of VSV is defined as a $LD_{50}$ that is at least 100,000-fold greater than the $LD_{50}$ of wild-type VSV, wherein the $LD_{50}$ is determined in an animal neurovirulence model. The determination of a 50% lethal dose ($LD_{50}$) for a particular VSV vector is readily determined by a person of skill in the art using known testing methods and animal models (e.g., see Example 1).

Thus, in certain embodiments, the invention is directed to a genetically modified VSV comprising at least two different classes of mutations set forth below.

1. Gene Shuffling Mutations

In certain embodiments, a genetically modified VSV of the invention comprises a gene shuffling mutation in its genome. As defined herein, the terms "gene shuffling", "shuffled gene", "shuffled", "shuffling", "gene rearrangement" and "gene translocation" are used interchangeably, and refer to a change (mutation) in the order of the wild-type VSV genome. As defined herein, a wild-type VSV genome has the following gene order: 3'-NPMGL-5'.

It is known in the art, that the position of a VSV gene relative to the 3' promoter determines the level of expression and virus attenuation (U.S. Pat. No. 6,596,529 and Wertz et al., 1998, each specifically incorporated herein by reference). The nucleotide sequences encoding VSV G, M, N, P and L proteins are known in the art (Rose and Gallione, 1981; Gallione et al., 1981). For example, U.S. Pat. No. 6,596,529 describes gene shuffling mutations in which the gene for the N protein is translocated (shuffled) from its wild-type promoter-proximal first position to successively more distal positions on the genome (e.g., 3'-PNMGL-5', 3'-PMNGL-5', 3'-PMGNL-5', referred to as N2, N3 and N4, respectively). Thus, in certain embodiments, a genetically modified VSV comprises a gene shuffling mutation in its genome. In one class of mutation, in one particular embodiment, a genetically modified VSV comprises a gene shuffling mutation comprising a translocation of the N gene (e.g., 3'-PNMGL-5' or 3'-PMNGL-5').

It should be noted herein, that the insertion of a foreign nucleic acid sequence (e.g., HIV gag) into the VSV genome 3' to any of the N, P, M, G or L genes, effectively results in a "gene shuffling mutation" as defined above. For example, when the HIV gag gene is inserted into the VSV genome at position one (e.g., 3'-$gag_1$-NPMGL-5'), the N, P, M, G and L genes are each moved from their wild-type positions to more distal positions on the genome. Thus, in certain embodiments of the invention, a gene shuffling mutation includes the insertion of a foreign nucleic acid sequence into the VSV genome 3' to any of the N, P, M, G or L genes (e.g., 3'-$gag_1$-NPMGL-5', 3'-N-$gag_2$-PMGL-5', 3'-NP-$gag_3$-MGL-5', etc.)

2. G Protein Insertion and Truncation Mutants

In certain other embodiments, a genetically modified VSV of the invention comprises a mutated G gene, wherein the encoded G protein is truncated at its cytoplasmic domain (carboxy-terminus), also referred to as the "cytoplasmic tail region" of the G protein. It is known in the art that G gene mutations which truncate the carboxy-terminus of the cytoplasmic domain influence VSV budding and attenuate virus production (Schnell et al., 1998; Roberts et al., 1999). The cytoplasmic domain of wild-type VSV G protein comprises twenty-nine amino acids (RVGIHLCIKLKHTKKRQIYT-DIEMNRLGK-COOH; SEQ ID NO:1).

In certain embodiments, a truncated VSV G gene of the invention encodes a G protein in which the last twenty-eight carboxy-terminal amino acid residues of the cytoplasmic domain are deleted (retaining only arginine from the twenty-nine amino acid wild-type cytoplasmic domain of SEQ ID NO:1). In certain other embodiments, a truncated VSV G gene of the invention encodes a G protein in which the last twenty carboxy-terminal amino acid residues of the cytoplasmic domain are deleted (relative to the twenty-nine amino acid wild-type cytoplasmic domain of SEQ ID NO:1).

In certain other embodiments, a truncated VSV G gene of the invention encodes a G protein comprising a single amino acid in its cytoplasmic domain (cytoplasmic tail region), wherein the single amino acid is any naturally occurring amino acid. In still other embodiments, a truncated VSV G gene of the invention encodes a G protein comprising nine amino acids in its cytoplasmic domain (cytoplasmic tail region), wherein the nine amino acids are any naturally occurring amino acids. In certain other embodiments, a mutated VSV gene of the invention encodes a G protein containing an insertion representing a foreign epitope. Such mutants are known in the art (e.g., see Schlehuber and Rose, 2003).

As defined herein, a G gene mutant encoding a G protein in which the last twenty-eight carboxy-terminal amino acid residues of the cytoplasmic domain are deleted, relative to the wild-type sequence of SEQ ID NO:1, is designated "$G_{(ct-1)}$", wherein the cytoplasmic domain of the $G_{(ct-1)}$ has an amino acid sequence of (R—COOH). As defined herein, a G gene mutant encoding a G protein in which the last twenty carboxy-terminal amino acid residues of the cytoplasmic domain are deleted, relative to the wild-type sequence of SEQ ID NO:1, is designated "$G_{(ct-9)}$", wherein the cytoplasmic domain of the $G_{(ct-9)}$ has an amino acid sequence of (RVGIHLCIK-COOH; SEQ ID NO:2). Thus, in certain embodiments of the invention, a genetically modified VSV of the invention comprises a mutated G gene, wherein the encoded G protein is a $G_{(ct-1)}$ or $G_{(ct-9)}$.

3. Temperature-sensitive and Other Point Mutations

A VSV "temperature-sensitive" ("ts") mutation, as defined hereinafter, is a mutation in the VSV genome which restricts VSV growth at a non-permissive temperature. For example, a VSV ts mutant of the invention grows normally and to high titer at the permissive temperature (e.g., 31° C.), but their growth or reproduction is restricted at non-permissive temperatures (e.g., 37° C. or 39° C.). The generation of ts mutants by chemical and site directed mutagenesis are well known in the art (e.g., see Pringle, 1970; Li et al., 1988); and numerous ts mutants have been characterized and described (e.g., see Flamand and Pringle, 1971; Flamand and Bishop, 1973; Printz and Wagner, 1971; Gopalakrishna and Lenard, 1985; Pringle et al., 1981; Morita et al., 1987; Li et al., 1988; Rabinowitz et al., 1977; Lundh et al., 1988; Dal Canto et al., 1976; Rabinowitz et al., 1976). In certain embodiments, a genetically modified VSV of the invention comprises a ts mutation in its genome, wherein the ts mutation is one or more mutations of a nucleic acid sequence encoding the G, M, N, P or L protein.

As defined herein, a ts mutation of any one the VSV G, M, N, P or L genes is a separate "mutation class" of the invention. For example, in certain embodiments of the invention, a genetically modified VSV comprising at least two different classes of mutations in its genome (wherein the two mutations synergistically attenuate VSV pathogenicity) comprises one or more ts N gene mutation(s) (hereinafter, "$N_{(ts)}$") as a first class of mutation and one or more ts L gene mutation(s) (hereinafter, "$L_{(ts)}$") as a second class of mutation. As a non-limiting example, a genetically modified VSV comprising a genome such as 3'-$N_{(ts)}$PMG$L_{(ts)}$-5' comprises two classes of mutations (i.e., (1) an $N_{(ts)}$ gene mutation and (2) an $L_{(ts)}$ gene mutation) and a genetically modified VSV comprising a genome such as 3'-$gag_1$-$N_{(ts)}$PMG$L_{(ts)}$-5' comprises three classes of mutations (i.e., (1) an $N_{(ts)}$ gene mutation, (2) an $L_{(ts)}$ gene mutation and (3) by way $gag_1$ insertion, a gene shuffling mutation).

In certain other embodiments, a genetically modified VSV of the invention comprises a point mutation in its genome, wherein the point mutation is one or more mutations of a nucleic acid sequence encoding the G, M, N, P or L protein, wherein the mutation confers an attenuating phenotype such as cold-adaptation, decreased fusion or cytopathogenic efficiency (e.g., see Fredericksen and Whitt, 1998; Ahmed and Lyles, 1997). For example, Fredericksen and Whitt (1998) describe three attenuating point mutations of the G gene (e.g., D137-L, E139-L or DE-SS) which have a shifted pH threshold for fusion activity. Ahmed and Lyles (1997) described an attenuating point mutation of the M gene (N1 63D) that was highly defective in inhibition of host gene expression and was turned over more rapidly than wild-type M protein. Thus, in certain embodiments, a genetically modified VSV of the invention comprises one or more point mutations in its genome.

4. Non-cytopathic M Gene Mutations

In certain other embodiments, a genetically modified VSV of the invention comprises a non-cytopathic mutation in the M gene. The VSV (Indiana serotype) M gene encodes a 229 amino acid M (matrix) protein, wherein the first thirty amino acids of the $NH_2$-terminus comprise a proline-rich PPPY (PY) motif (Harty et al., 1999). The PY motif of VSV M protein is located at amino acid positions 24-27 in both VSV Indiana (Genbank Accession Number X04452) and New Jersey (Genbank Accession Number M14553) serotypes. It was demonstrated by Jayakar et al. (2000), that mutations in the PY motif (e.g., APPY, AAPY, PPAY, APPA, AAPA and PPPA) reduce virus yield by blocking a late stage in virus budding. Thus, in certain embodiments, a genetically modified VSV of the invention comprises a non-cytopathic mutation in the M gene, wherein the mutation is in the PPPY motif of the encoded M protein.

It has recently been reported that the M mRNA further encodes two additional proteins, referred to as M2 and M3 (Jayakar and Whitt, 2002). The M2 and M3 proteins are synthesized from downstream methionines in the same reading frame that encodes the 229 amino acid M protein (referred to as M1), and lack the first thirty-two (M2 protein) or fifty (M3 protein) amino acids of the M1 protein. It has been observed that cells infected with a recombinant VSV that expresses the M protein, but not M2 and M3, exhibit a delayed onset of cytopathic effect (in certain cell types), yet produce a normal virus yield. Thus, in certain embodiments, a genetically modified VSV of the invention comprises a non-cytopathic mutation in the M gene, wherein the M gene mutation results in a virus that does not express the M2 or M3 protein (e.g., see Jayakar and Whitt, 2002).

Also contemplated herein are amino acid mutations (e.g., deletions, substitutions, insertions, etc.) into the M protein PSAP (PS) motif described by Irie et al. (2004).

5. G-stem Mutations

In certain embodiments, a genetically modified VSV of the invention comprises a mutation in the G gene, wherein the encoded G protein has a mutation in the membrane-proximal stem region of the G protein ectodomain, referred to as G-stem protein. The G-stem region comprises amino acid residues 421 through 462 of the G protein. Recent studies have demonstrated the attenuation of VSV via insertion and/or deletion (e.g., truncation) mutations in the G-stem of the G protein (Robinson and Whitt, 2000; Jeetendra et al., 2002; Jeetendra et al., 2003). Thus, in certain embodiments, a genetically modified VSV comprises a G-stem insertion, deletion, substitution or a combination thereof. In one particular embodiment, a genetically modified VSV vector of the invention comprising a G-stem mutation (and immunogenic compositions thereof), comprises a genome of 3'-$gag_1$-NPM$G_{(stem)}$L-5'.

6. Ambisense RNA Mutations

In certain embodiments, a genetically modified VSV of the invention comprises an ambisense RNA mutation, in which the 5' antigenome promoter (AGP) is replaced with a copy of the 3' genome promoter (GP). The 5' AGP of VSV, as well as other nonsegmented, negative strand RNA viruses, acts as a strong replication promoter while the 3' GP acts as a transcription promoter and a weak replication promoter. In the normal course of VSV infection, there is a 3- to 4-fold predominance of genome copies over antigenome copies; this ratio is even higher for rabies virus, another member of the Rhabdovirus family (Finke and Conzelmann, 1999). Previous work with rabies virus demonstrated that replacing the 5' AGP with a copy of the GP (known as an ambisense RNA mutation) led to equal levels of genome and antigenome RNA copies within infected cells. In addition, a foreign gene was expressed from the copy of the GP placed at the 5' end of the genome. When serially passaged in cultured cells, the rabies virus containing the ambisense RNA mutation consistently replicated to 10- to 15-fold lower titers than a recombinant wild type rabies virus (Finke and Conzelmann, 1997). Such a mutation is used in VSV vectors to both attenuate the virus replication and express foreign genes. Thus, in certain embodiments, a genetically modified VSV comprises an ambisense RNA mutation.

7. Gene Deletions

In certain other embodiments, a genetically modified VSV of the invention comprises a virus in which a VSV gene (such as G or M) is deleted from the genome. For example, Roberts et al. (1999) described a VSV vector in which the entire gene encoding the G protein was deleted (ΔG) and substituted with influenza haemagglutinin (HA) protein, wherein the VSV vector (ΔG-HA) demonstrated attenuated pathogenesis.

B. Recombinant Vesicular Stomatitis Virus Vectors

In certain embodiments, the invention provides a genetically modified (recombinant) VSV vector comprising at least two different classes of mutations in its genome and at least one foreign RNA sequence inserted as a separate transcriptional unit into or replacing a region of the VSV genome non-essential for replication.

Methods of producing recombinant RNA virus are referred to in the art as "rescue" or "reverse genetics" methods. Exemplary rescue methods for VSV are described in U.S. Pat. Nos. 6,033,886, 6,596,529 and WO 2004/113517, each incorporated herein by reference. The transcription and replication of negative-sense, single stranded, non-segmented, RNA viral genomes are achieved through the enzymatic activity of a multimeric protein complex acting on the ribonucleoprotein core (nucleocapsid). Naked genomic RNA cannot serve as a template. Instead, these genomic sequences are recognized only when they are entirely encapsidated by the N protein into the nucleocapsid structure. It is only in that context that the genomic and antigenomic terminal promoter sequences are recognized to initiate the transcriptional or replication pathways.

A cloned DNA equivalent of the VSV genome is placed between a suitable DNA-dependent RNA polymerase promoter (e.g., the T7 RNA polymerase promoter) and a self-cleaving ribozyme sequence (e.g., the hepatitis delta ribozyme), which is inserted into a suitable transcription vector (e.g., a propagatable bacterial plasmid). This transcription vector provides the readily manipulable DNA template from which the RNA polymerase (e.g., T7 RNA polymerase) can faithfully transcribe a single-stranded RNA copy of the VSV antigenome (or genome) with the precise, or nearly precise, 5' and 3' termini. The orientation of the VSV genomic DNA copy and the flanking promoter and ribozyme sequences determine whether antigenome or genome RNA equivalents are transcribed. Also required for rescue of new VSV progeny are the VSV-specific trans-acting support proteins needed to encapsidate the naked, single-stranded VSV antigenome or genome RNA transcripts into functional nucleocapsid templates: the viral nucleocapsid (N) protein, the polymerase-associated phosphoprotein (P) and the polymerase (L) protein. These proteins comprise the active viral RNA-dependent RNA polymerase which must engage this nucleocapsid template to achieve transcription and replication.

Thus, a genetically modified and attenuated VSV of the invention, comprising at least two different classes of mutations in its genome (e.g., see Section A), is produced according to rescue methods known in the art. For example, a genetically modified VSV vector comprising at least two different classes of mutations in its genome is generated using (1) a transcription vector comprising an isolated nucleic acid molecule which comprises a polynucleotide sequence encoding a genome or antigenome of a VSV and (2) at least one expression vector which comprises at least one isolated nucleic acid molecule encoding the trans-acting N, P and L proteins necessary for encapsidation, transcription and replication; in a host cell under conditions sufficient to permit the co-expression of these vectors and the production of the recombinant VSV. Any suitable VSV strain or serotype may be used according to the present invention, including, but not limited to, VSV Indiana, VSV New Jersey, VSV Chandipura, VSV Isfahan, VSV San Juan, VSV Glasgow, and the like.

In addition to polynucleotide sequences encoding attenuated forms of VSV, the polynucleotide sequence may also encode one or more heterologous (or foreign) polynucleotide sequences or open reading frames (ORFs) (e.g., see Section C). The heterologous polynucleotide sequences can vary as desired, and include, but are not limited to, a co-factor, a cytokine (such as an interleukin), a T-helper epitope, a CTL epitope, a restriction marker, an adjuvant, or a protein of a different microbial pathogen (e.g. virus, bacterium, parasite or fungus), especially proteins capable of eliciting desirable immune responses. In certain embodiments, a heterologous ORF contains an HIV gene (e.g., gag, env, pol, vif, nef, tat, vpr, rev or vpu). In one particular embodiment, the HIV gene is gag, wherein the gag gene is inserted into the VSV genome at position one (3'-$gag_1$-NPMGL-5') or at position five (3'-NPMG-$gag_5$-L-5'). The heterologous polynucleotide is also used to provide agents which are used for gene therapy. In another embodiment, the heterologous polynucleotide sequence further encodes a cytokine, such as interleukin-12, which are selected to improve the prophylatic or therapeutic characteristics of the recombinant VSV.

In certain embodiments, a genetically modified and attenuated VSV of the invention is mutated by conventional means, such as chemical mutagenesis. For example, during virus growth in cell cultures, a chemical mutagen is added, followed by: (a) selection of virus that has been subjected to passage at suboptimal temperature in order to select temperature-sensitive and/or cold adapted mutations, (b) identification of mutant virus that produce small plaques in cell culture, and (c) passage through heterologous hosts to select for host range mutations. In other embodiments, attenuating mutations comprise making predetermined mutations using site-directed mutagenesis (e.g., see Section A) and then rescuing virus containing these mutations. As set forth previously, a genetically modified VSV of the invention comprises at least two classes of mutation in its genome. In certain embodiments, one or more classes of mutation further comprises multiple mutations, such as a G-stem mutation class having a double mutation (e.g., a deletion, insertion, substitution, etc.), a triple mutation and the like. These attenuated VSV vectors are then screened for attenuation of their virulence in an animal model (e.g., see Example 1 and Example 3).

The typical (although not necessarily exclusive) circumstances for rescue include an appropriate mammalian cell milieu in which T7 polymerase is present to drive transcription of the antigenomic (or genomic) single-stranded RNA from the viral genomic cDNA-containing transcription vector. Either co-transcriptionally or shortly thereafter, this viral antigenome (or genome) RNA transcript is encapsidated into functional templates by the nucleocapsid protein and engaged by the required polymerase components produced concurrently from co-transfected expression plasmids encoding the required virus-specific trans-acting proteins. These events and processes lead to the prerequisite transcription of viral mRNAs, the replication and amplification of new genomes and, thereby, the production of novel VSV progeny, i.e., rescue.

The transcription vector and expression vector are typically plasmid vectors designed for expression in the host cell. The expression vector which comprises at least one isolated nucleic acid molecule encoding the trans-acting proteins necessary for encapsidation, transcription and replication expresses these proteins from the same expression vector or at least two different vectors. These vectors are generally known from the basic rescue methods, and they need not be altered for use in the improved methods of this invention.

Additional techniques for conducting rescue of viruses such as VSV, are described in U.S. Pat. No. 6,673,572 and U.S. Provisional Patent 60/477,389, which are hereby incorporated by reference.

The host cells used in the rescue of VSV are those which permit the expression from the vectors of the requisite constituents necessary for the production of recombinant VSV. Such host cells can be selected from a prokaryotic cell or a eukaryotic cell, and preferably a vertebrate cell. In general, host cells are derived from a human cell, such as a human embryonic kidney cell (e.g., 293). Vero cells, as well as many other types of cells are also used as host cells. The following are non-limiting examples of suitable host cells: (1) Human Diploid Primary Cell Lines (e.g. WI-38 and MRC5 cells); (2) Monkey Diploid Cell Line (e.g. FRhL-Fetal Rhesus Lung cells); (3) Quasi-Primary Continues Cell Line (e.g. AGMK-African green monkey kidney cells); (4) Human 293 cells and (5) other potential cell lines, such as, CHO, MDCK (Madin- Darby Canine Kidney), primary chick embryo fibroblasts. In certain embodiments, a transfection facilitating reagent is added to increase DNA uptake by cells. Many of these reagents are known in the art (e.g., calcium phosphate). Lipofectace (Life Technologies, Gaithersburg, Md.) and Effectene (Qiagen, Valencia, Calif.) are common examples. Lipofectace and Effectene are both cationic lipids. They both coat DNA and enhance DNA uptake by cells. Lipofectace forms a liposome that surrounds the DNA while Effectene coats the DNA but does not form a liposome.

The rescued attenuated VSV is then tested for its desired phenotype (temperature sensitivity, cold adaptation, plaque morphology, and transcription and replication attenuation), first by in vitro means. The mutations are also tested using a minireplicon system where the required trans-acting encapsidation and polymerase activities are provided by wild-type or vaccine helper viruses, or by plasmids expressing the N, P and different L genes harboring gene-specific attenuating mutations. The attenuated VSV is also tested in vivo for synergistic attenuation in an animal neurovirulence model. For example, mouse and/or ferret models are established for detecting neurovirulence. Briefly, groups of ten mice are injected intracranially (IC) with each of a range of virus concentrations that span the anticipated $LD_{50}$ dose (a dose that is lethal for 50% of animals). For example, IC inoculations with virus at $10^2$, $10^3$, $10^4$ and $10^5$ pfu are used where the anticipated $LD_{50}$ for the virus is in the range $10^3$-$10^4$ pfu. Virus formulations are prepared by serial dilution of purified virus stocks in PBS. Mice are then injected through the top of the cranium with the requisite dose, in 50-100 μl of PBS. Animals are monitored daily for weight loss, morbidity and death. The $LD_{50}$ for a virus vector is then calculated from the cumulative death of mice over the range of concentrations tested.

C. Heterologous Nucleic Acid Sequences and Antigens

In certain embodiments, the invention provides synergistically attenuated VSV further comprising a foreign RNA sequence as a separate transcriptional unit inserted into or replacing a site of the genome nonessential for replication, wherein the foreign RNA sequence (which is in the negative sense) directs the production of a protein capable of being expressed in a host cell infected by VSV. This recombinant genome is originally produced by insertion of foreign DNA encoding the protein into the VSV cDNA. In certain embodiments, any DNA sequence which encodes an immunogenic antigen, which produces prophylactic or therapeutic immunity against a disease or disorder, when expressed as a fusion or non-fusion protein in a recombinant synergistically attenuated VSV of the invention, alone or in combination with other antigens expressed by the same or a different VSV, is isolated and incorporated in the VSV vector for use in the immunogenic compositions of the present invention.

In certain embodiments, expression of an antigen by a synergistically attenuated recombinant VSV induces an immune response against a pathogenic microorganism. For example, an antigen may display the immunogenicity or antigenicity of an antigen found on bacteria, parasites, viruses, or fungi which are causative agents of diseases or disorders. In one embodiment, antigens displaying the antigenicity or immunogenicity of an antigen of a human pathogen or other antigens of interest are used.

To determine immunogenicity or antigenicity by detecting binding to antibody, various immunoassays known in the art are used, including but not limited to, competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, neutralization assays, etc. In one embodiment, antibody binding is measured by detecting a label on the primary antibody. In another embodiment, the primary antibody is detected by measuring binding of a secondary antibody or reagent to the primary antibody. In a further embodiment, the secondary antibody is labeled. Many means are known in the art for detecting binding in an immunoassay. In one embodiment for detecting immunogenicity, T cell-mediated responses are assayed by standard methods, e.g., in vitro or in vivo cytoxicity assays, tetramer assays, elispot assays or in vivo delayed-type hypersensitivity assays.

Parasites and bacteria expressing epitopes (antigenic determinants) that are expressed by synergistically attenuated VSV (wherein the foreign RNA directs the production of an antigen of the parasite or bacteria or a derivative thereof containing an epitope thereof) include but are not limited to those listed in Table 1.

TABLE 1

PARASITES AND BACTERIA EXPRESSING EPITOPES
THAT CAN BE EXPRESSED BY VSV

| PARASITES |
| --- |
| *plasmodium* spp. |
| *Eimeria* spp. |
| nematodes |
| schisto |
| leshmania |
| BACTERIA |
| *Vibrio cholerae* |
| *Streptococcus pneumoniae* |
| *Streptococcus agalactiae* |
| *Neisseria meningitidis* |
| *Neisseria gonorrheae* |
| *Corynebacteria diphtheriae* |
| *Clostridium tetani* |
| *Bordetella pertussis* |
| *Haemophilus* spp. (e.g., *influenzae*) |
| *Chlamydia* spp. |
| Enterotoxigenic *Escherichia coli* |
| *Helicobacter pylori* |
| mycobacteria |

In another embodiment, the antigen comprises an epitope of an antigen of a nematode, to protect against disorders caused by such worms. In another embodiment, any DNA sequence which encodes a Plasmodium epitope, which when expressed by a recombinant VSV, is immunogenic in a vertebrate host, is isolated for insertion into VSV (−) DNA according to the present invention. The species of Plasmodium which serve as DNA sources include, but are not limited to, the human malaria parasites *P. falciparum, P. malariae, P. ovale, P. vivax*, and the animal malaria parasites *P. berghei, P. yoelii, P. knowlesi*, and *P. cynomolgi*. In yet another embodiment, the antigen comprises a peptide of the β-subunit of Cholera toxin.

Viruses expressing epitopes that are expressed by synergistically attenuated VSV (wherein the foreign RNA directs the production of an antigen of the virus or a derivative thereof comprising an epitope thereof) include, but are not limited to, those listed in Table 2, which lists such viruses by family for purposes of convenience and not limitation.

TABLE 2

VIRUSES EXPRESSING EPITOPES THAT CAN BE EXPRESSED BY VSV

I. Picornaviridae

Enteroviruses
Poliovirus
Coxsackievirus
Echovirus
Rhinoviruses
Hepatitis A Virus II. Caliciviridae Norwalk group of viruses III. Togaviridae and Flaviviridae Togaviruses (e.g., Dengue virus)
Alphaviruses
Flaviviruses (e.g., Hepatitis C virus)
Rubella virus IV. Coronaviridae Coronaviruses V. Rhabdoviridae Rabies virus VI. Filoviridae Marburg viruses
Ebola viruses VII. Paramyxoviridae Parainfluenza virus
Mumps virus
Measles virus
Respiratory syncytial virus
Metapneumovirus VIII. Orthomyxoviridae Orthomyxoviruses (e.g., Influenza virus)

IX. Bunyaviridae

Bunyaviruses

X. Arenaviridae

Arenaviruses

XI. Reoviridae

Reoviruses
Rotaviruses
Orbiviruses

XII. Retroviridae

Human T Cell Leukemia Virus type I
Human T Cell Leukemia Virus type II
Human Immunodeficiency Viruses (e.g., type 1 and type II)
Simian Immunodeficiency Virus
Lentiviruses XIII. Papoviridae Polyomaviruses
Papillomaviruses XIV. Parvoviridae Parvoviruses XV. Herpesviridae Herpes Simplex Viruses
Epstein-Barr virus
Cytomegalovirus
Varicella-Zoster virus
Human Herpesvirus-6
human herpesvirus-7
Cercopithecine Herpes Virus 1 (B virus)

TABLE 2-continued

VIRUSES EXPRESSING EPITOPES THAT CAN BE EXPRESSED BY VSV

XVI. Poxviridae

Poxviruses

XVIII. Hepadnaviridae

Hepatitis B virus

XIX. Adenoviridae

In specific embodiments, the antigen encoded by the foreign sequences that is expressed upon infection of a host by the attenuated VSV, displays the antigenicity or immunogenicity of an influenza virus hemagglutinin; human respiratory syncytial virus G glycoprotein (G); measles virus hemagglutinin or herpes simplex virus type-2 glycoprotein gD.

Other antigens that are expressed by attenuated VSV include, but are not limited to, those displaying the antigenicity or immunogenicity of the following antigens: Poliovirus I VP1; envelope glycoproteins of HIV I; Hepatitis B surface antigen; Diphtheria toxin; streptococcus 24M epitope, SpeA, SpeB, SpeC or C5a peptidease; and gonococcal pilin.

In other embodiments, the antigen expressed by the attenuated VSV displays the antigenicity or immunogenicity of pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulina hydodysenteriae protective antigen, Bovine Viral Diarrhea glycoprotein 55, Newcastle Disease Virus hemagglutinin-neuraminidase, swine flu hemagglutinin, or swine flu neuraminidase.

In certain embodiments, an antigen expressed by the attenuated VSV displays the antigenicity or immunogenicity of an antigen derived from a canine or feline pathogen, including, but not limited to, feline leukemia virus, canine distemper virus, canine adenovirus, canine parvovirus and the like.

In certain other embodiments, the antigen expressed by the attenuated VSV displays the antigenicity or immunogenicity of an antigen derived from Serpulina hyodysenteriae, Foot and Mouth Disease Virus, Hog Colera Virus, swine influenza virus, African Swine Fever Virus, Mycoplasma hyopneumoniae, infectious bovine rhinotracheitis virus (e.g., infectious bovine rhinotracheitis virus glycoprotein E or glycoprotein G), or infectious laryngotracheitis virus (e.g., infectious laryngotracheitis virus glycoprotein G or glycoprotein I).

In another embodiment, the antigen displays the antigenicity or immunogenicity of a glycoprotein of La Crosse Virus, Neonatal Calf Diarrhea Virus, Venezuelan Equine Encephalomyelitis Virus, Punta Toro Virus, Murine Leukemia Virus or Mouse Mammary Tumor Virus.

In other embodiments, the antigen displays the antigenicity or immunogenicity of an antigen of a human pathogen, including but not limited to human herpesvirus, herpes simplex virus-1, herpes simplex virus-2, human cytomegalovirus, Epstein-Barr virus, Varicella-Zoster virus, human herpesvirus-6, human herpesvirus-7, human influenza virus, human immunodeficiency virus (type 1 and/or type 2), rabies virus, measles virus, hepatitis B virus, hepatitis C virus, *Plasmodium falciparum*, and *Bordetella pertussis*.

Potentially useful antigens or derivatives thereof for use as antigens expressed by attenuated VSV are identified by various criteria, such as the antigen's involvement in neutralization of a pathogen's infectivity, type or group specificity, recognition by patients' antisera or immune cells, and/or the demonstration of protective effects of antisera or immune cells specific for the antigen.

In another embodiment, foreign RNA of the attenuated VSV directs the production of an antigen comprising an epitope, which when the attenuated VSV is introduced into a desired host, induces an immune response that protects against a condition or disorder caused by an entity containing the epitope. For example, the antigen can be a tumor specific antigen or tumor-associated antigen, for induction of a protective immune response against a tumor (e.g., a malignant tumor). Such tumor-specific or tumor-associated antigens include, but are not limited to, KS 1/4 pan-carcinoma antigen; ovarian carcinoma antigen (CA125); prostatic acid phosphate; prostate specific antigen; melanoma-associated antigen p97; melanoma antigen gp75; high molecular weight melanoma antigen and prostate specific membrane antigen.

The foreign DNA encoding the antigen, that is inserted into a non-essential site of the attenuated VSV DNA, optionally further comprises a foreign DNA sequence encoding a cytokine capable of being expressed and stimulating an immune response in a host infected by the attenuated VSV. For example, such cytokines include but are not limited to interleukins $1\alpha$, $1\beta$, 2, 4, 5, 6, 7, 8, 10, 12, 13, 14, 15, 16, 17 and 18, interferon-$\alpha$, interferon-$\beta$, interferon-$\gamma$, granulocyte colony stimulating factor, granulocyte macrophage colony stimulating factor and the tumor necrosis factors $\alpha$ and $\beta$.

D. Immunogenic and Pharmaceutical Compositions

In certain embodiments, the invention is directed to an immunogenic composition comprising an immunogenic dose of a genetically modified VSV vector comprising at least two different classes of mutations in its genome and at least one foreign RNA sequence inserted into or replacing a region of the VSV genome non-essential for replication, wherein the two mutations synergistically attenuate VSV pathogenicity.

The synergistically attenuated VSV vectors of the invention are formulated for administration to a mammalian subject (e.g., a human). Such compositions typically comprise the VSV vector and a pharmaceutically acceptable carrier. As used hereinafter the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the VSV vector, such media are used in the immunogenic compositions of the invention. Supplementary active compounds may also be incorporated into the compositions.

Thus, a VSV immunogenic composition of the invention is formulated to be compatible with its intended route of administration. Examples of routes of administration include parenteral (e.g., intravenous, intradermal, subcutaneous, intramuscular, intraperitoneal) and mucosal (e.g., oral, rectal, intranasal, buccal, vaginal, respiratory). Solutions or suspensions used for parenteral, intradermal, or subcutaneous application include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH is adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier is a solvent or dispersion medium containing, for example, water, ethanol, polyol (e.g., glycerol, propylene glycol, and liquid polyetheylene glycol, and the like), and suitable mixtures thereof. The proper fluidity is maintained, for example, by the use of a coating such as lecithin, by the maintenance of the required particle size in the case of dispersion and by the use of surfactants. Prevention of the action of microorganisms is achieved by various antibacterial and antifungal agents, for example, parabens, chlorobutanol, phenol, ascorbic acid, and the like. In many cases, it is preferable to include isotonic agents, for example, sugars, polyalcohols such as manitol, sorbitol, sodium chloride in the composition. Prolonged absorption of the injectable compositions is brought about by including in the composition an agent which delays absorption, for example, aluminum monostearate and gelatin.

Sterile injectable solutions are prepared by incorporating the VSV vector in the required amount (or dose) in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For administration by inhalation, the compounds are delivered in the form of an aerosol spray from pressured container or dispenser which contains a suitable propellant (e.g., a gas such as carbon dioxide, or a nebulizer). Systemic administration can also be by mucosal or transdermal means. For mucosal or transdermal administration, penetrants appropriate to the barrier to be permeated are used in the formulation. Such penetrants are generally known in the art, and include, for example, for mucosal administration, detergents, bile salts, and fusidic acid derivatives. Mucosal administration is accomplished through the use of nasal sprays or suppositories. The compounds are also prepared in the form of suppositories (e.g., with conventional suppository bases such as cocoa butter and other glycerides) or retention enemas for rectal delivery.

In certain embodiments, it is advantageous to formulate oral or parenteral compositions in dosage unit form for ease of administration and uniformity of dosage. Dosage unit form as used hereinafter refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

All patents and publications cited herein are hereby incorporated by reference.

D. EXAMPLES

The following examples are carried out using standard techniques, which are well known and routine to those of skill in the art, except where otherwise described in detail. The following examples are presented for illustrative purpose, and should not be construed in any way limiting the scope of this invention.

Example 1

Materials and Methods

VSV G Protein Cytoplasmic Tail Mutants

The methods used for the generation of G protein cytoplasmic tail mutants of the present invention are known in the art and described in detail by Schnell et al., (1998). These G protein mutants retained either a single amino acid ($G_{(ct-1)}$) or nine amino acids ($G_{(ct-9)}$) in the G cytoplasmic tail domain compared to the twenty-nine amino acid cytoplasmic tail domain of wild type VSV Indiana strain (SEQ ID NO:1). The cytoplasmic tail truncations were generated by moving the translation stop codon either 60 nucleotides or 84 nucleotides (i.e., nine amino acid cytoplasmic tail and one amino acid cytoplasmic tail, respectively) upstream of the authentic stop codon and resulting in truncation of the G protein.

VSV N Gene Shuffled Mutants

The N gene translocation mutants (N shuffles) were generated by repositioning the N gene as either the second, third or fourth gene from the 3' end of the virus genome. For example the authentic gene order for wild-type VSV, 3'-NP-MGL-5', was mutated to 3'-PNMGL-5' and 3'-PMNGL-5'. Translocation of the N gene further away from the unique 3' RNA transcription promoter causes a proportionate drop in the level of N gene expression (e.g., see U.S. Pat. No. 6,596,529, specifically incorporated herein by reference in its entirety). A reduction in the level of N protein in infected cells slows the formation of viral nucleocapsid formation, ultimately reducing the rate of genome replication and virus particle formation. The methods used for N gene translocations are described below.

For the first step in the production of the N gene shuffles, the N gene was removed entirely from the full-length virus genome cDNA, with the result that the P gene was then immediately adjacent to the virus leader, in place of the N gene. To delete the N gene, two PCR products were made with a full-length genome cDNA as template. The first PCR product contained sequence stretching from a natural BsaAI site upstream of the T7 promoter, to the end of the virus leader and an added downstream BsmBI site. The second PCR product contained sequence stretching from the natural XbaI site in the P gene to the transcription start signal for the P gene, adjacent to an added upstream BsmBI site. The BsmBI sites were arranged in a way that both PCR products could be joined seamlessly (following digestion and ligation) to give a single DNA fragment that contained the virus leader immediately adjacent to the P gene. This DNA fragment was then ligated into the XbaI/BsaAI sites of full-length genome cDNA, effectively eliminating the N gene from the virus genome.

In the next step of the generation of N gene shuffles, the N gene was inserted between either the P and M genes, or the M and G genes, or the G and L genes of the deleted N genome cDNA. For insertion of the N gene between the P and M genes, three PCR products were prepared with full-length genome cDNA as template. The first PCR product contained sequence stretching from the natural XbaI site in the P gene, to the transcription start signal of the M gene, with an added flanking BsmBI site. The second PCR product contained sequence stretching from the transcription start signal of the N gene to the conserved TATG sequence adjacent to the 3'-AAAAAAA-polyadenylation signal in the N gene, with an added flanking BsmBI site. The third PCR product contained sequence stretching from the natural MluI site at the beginning of the G gene to the conserved TATGAAAAAAA polyadenylation signal (SEQ ID NO: 3) of the P gene, with an added flanking BsmBI site. All three fragments were then digested with BsmBI, and religated to form a single DNA fragment with the N gene flanked by part of the P gene and the M gene. This DNA fragment was then digested with XbaI and MluI and ligated into the XbaI/MluI sites of the delta-N virus genome to form the 3'-PNMGL-5' cDNA.

To generate the 3'-PMNGL-5' genome cDNA, two separate PCR products were prepared. The first PCR product contained sequence stretching from the natural XbaI site in the P gene to the transcription start signal (5'-AACAG-3') of the G gene, with an added flanking BsmBI site. The second PCR product contained the entire N gene sequence from the transcription start signal, with an added flanking upstream BsmBI site, to the N gene transcription stop/polyadenylation signal, with flanking sequence stretching from the G transcription start signal to the natural MluI site in the G gene. The G gene specific sequence was added to the N gene sequence as part of one of the PCR primers. Both PCR products were digested with BsmBI and ligated to form a single DNA fragment, which was then digested with XbaI and MluI and ligated into the XbaI/MluI sites of the deleted N genome cDNA to give a 5'-PMNGL-3' gene arrangement.

To generate a 5'-PMGNL-5' genome cDNA, three PCR products were prepared from a complete genome cDNA template. The first PCR product contained sequence stretching from the natural SwaI site in the G gene to the transcription start signal for the L gene, flanked by an added BsmBI site. The second PCR product contained sequence for the entire N gene, from transcription start signal to transcription stop signal, flanked at both ends by added BsmBI sites. The third PCR product contained sequence stretching from the L gene transcription start, flanked by an added BsmBI site, to a natural HpaI site in the L gene. All three PCR products were digested with BsmBI and ligated to form a single DNA fragment, which was then digested with SwaI and HpaI, and ligated into the SwaI/HpaI sites of the deleted N genome cDNA, resulting in a 5'-PMGNL-3' gene arrangement. In all three rearranged genomes the sequence-integrity of each gene and flanking regulatory sequences were identical to the unaltered virus; only the position of the N gene was different.

Combination of G Protein Cytoplasmic Tail Mutations and N Shuffle Mutations

The combination of both the N gene shuffles and the G protein cytoplasmic tail truncations resulted in doubly mutated genomes (i.e., two mutation classes), for example 3'-PNMG$_{(ct-9)}$L-5', 3'-PNMG$_{(ct-1)}$L-5', and 3'-PMNG$_{(ct-9)}$L-5', 3'-PMNG$_{(ct-1)}$L-5'. The double mutant genome cDNAs were constructed by swapping the natural G gene in the N shuffled genomes, with either the truncated $G_{(ct-1)}$ or $G_{(ct-9)}$ genes described above. The swap was performed by digestion of donor cDNAs (5'-NPM $G_{(ct-1)}$L-3' and 5'-NPM $G_{(ct-9)}$L-3') with MluI and HpaI, followed by ligation of the purified, truncated G genes into the MluI/HpaI sites of the N shuffled cDNA genomes. These double mutants were rescued from cDNA, triple plaque purified, amplified and characterized in cell culture by plaque size and growth kinetics as described below.

Non-Cytopathic M Gene Mutations

The VSV M gene encodes the virus matrix (M) protein, and two smaller in-frame polypeptides (M2 and M3). The M2 and M3 polypeptides are translated from the same open reading frame (ORF) as the M protein, and lack the first 33 and 51 amino acids respectively. A recombinant VSV vector comprising non-cytopathic M gene mutations (i.e., VSV vectors that also do not express M2 and M3 proteins) was generated as described below, and further comprised one or more additional mutation(s) thereby resulting in a VSV vector that was highly attenuated in cell culture and in animals.

The non-cytopathic M gene mutations ($M_{(ncp)}$), which result in the conversion of methionines 33 and 51 to alanines (M33A, M51A) were generated using a PCR based cloning strategy, where the necessary nucleotide substitutions (AUG to GCT) were incorporated into the PCR primers (Jayakar and Whitt, 2002; Jayakay et al., 2000). The resulting PCR products containing the M33,51A mutations were then cloned into the full length VSV cDNA genome, allowing rescue of virus that does not express M2 and M3 polypeptides.

The M33,51A mutations present in the recombinant VSV vector cDNA designed by Jayakar and Whitt, were transferred to the VSV vector(s) cDNA by exchanging the XbaI-MluI fragment (spanning the entire M gene and part of the P gene). The cDNA fragment swap did not result in any additional amino acid coding changes over and above the M33, 51A mutations.

Combination of G Protein Cytoplasmic Tail Mutations and Non-Cytopathic M Gene Mutations The combination of both the G protein cytoplasmic tail truncations and non-cytopathic M gene mutations resulted in doubly mutated genomes (i.e., two mutation classes), for example 3'-NPMncpGct-1L-5' or 3'-NPMncpGct-9L-5'. The double mutant genome cDNA's were constructed by swapping M gene cDNA containing the mutations that give rise to the non-cytopathic phenotype, into full length genome cDNA that contained either $G_{(ct-1)}$ or $G_{(ct-9)}$ mutations. In each case, the swapped cDNA fragment stretched from the unique Xba I site in the P gene to the unique Mlu I site in the 5' non-translated region of the G gene, and included the entire non-cytopathic M gene sequence.

As described previously the non-cytopathic M protein differed from the M protein it replaced, by only two amino acid substitutions (M33A and M51A), which give rise to the non-cytopathic phenotype. These doubly mutated genomes were then further modified by insertion of the HIV-1 gag gene at position 5 in the genome, between the G and L genes, to permit expression of gag protein for immunogenicity studies. As for other virus rVSV vectors the gag gene was cloned into the unique Xho I/Nhe I sites at position 5 of the genome cDNA.

VSV N Gene Temperature Sensitive Mutations and/or VSV L Gene Temperature Sensitive Mutations A recombinant VSV (rVSV) encoding HIV Gag protein from the first 3' cistron in the viral genome (rVSV-Gag$_1$) was modified by replacing the N gene and/or L gene with homologous coding sequences derived from known biologically-derived VSV temperature sensitive (ts) mutants (Pringle, 1970). The resulting vectors, (i) rVSV-Gag$_1$tsN (i.e., 3'-gag$_1$-N$_{(ts)}$PMGL-5') contained the ts N gene from VSV strain ts41, (ii) rVSV-Gag$_1$tsL (i.e., 3'-gag$_1$-NPMGL$_{(ts)}$-5') contained the L gene from VSV strain ts11 and (iii) rVSV-Gag$_1$tsN+L (i.e., 3'-gag$_1$-N$_{(ts)}$PMGL$_{(ts)}$-5') contained both the ts N gene from VSV strain ts41 and the L gene from VSV strain ts11. VSV strains ts41 and ts11 are also known in the art as tsG41 and tsG11, respectively.

Both biologically-derived ts gene-donor strains were isolated by Pringle (Pringle, 1970) after subjecting a laboratory-adapted VSV (the Glasgow strain of the Indiana Serotype) to chemical mutagenesis. Pringle also mapped the ts mutations to the N or L gene.

The ts41 N and ts11 L genes were cloned from infected-cell RNA. Briefly, BHK cells were infected with ts11 or ts41 at permissive temperature (31-32° C.). The infection was allowed to proceed until cytopathic effect was evident in more than 75% of the cell monolayer, at which time total RNA was extracted and purified. The RNA then was reverse-transcribed using gene-specific primers to direct cDNA synthesis after which the cDNA was amplified by PCR. The amplified cDNAs were then cloned into the rVSV vector genomic cDNA and verified by sequence analysis.

The complete genomic sequence of ts11, ts41, and their progenitor strain (Glasgow) was determined to identify coding changes that contribute to the ts phenotype. By comparing coding sequences from the rVSV vector background, the Pringle ts mutants, and the Glasgow progenitor virus, it is possible to predict which coding changes contribute to the ts phenotypes of rVSV-Gag$_1$tsN, rVSV-Gag$_1$tsL and rVSV-Gag$_1$tsN+L vectors.

Table 3 is a comparison of N protein amino acid sequences. It is apparent from the data, that replacement of the rVSV vector N gene with the ts41 homolog resulted in 4 amino acid substitutions. Any of these changes may affect N protein function in the context of the vector genetic background and contribute to the ts phenotype. It was notable that only one change (Tyr to Cys at position 74, residues shown in italics) distinguished ts41 from its progenitor virus (Glasgow), suggesting that this substitution may be a critical ts determinant.

TABLE 3

COMPARISON OF VSV N PROTEINS

| Amino Acid No. | Virus Strain | | |
|---|---|---|---|
| | XN2 | ts41 | Glasgow |
| 14 | Val | Ile | Ile |
| 74 | Tyr | *Cys* | *Tyr* |
| 128 | Ser | Arg | Arg |
| 353 | Asn | Ser | Ser |

Similarly, Table 4 provides the L protein comparison. Replacement of the L gene in the rVSV vector with the ts11 counterpart resulted in 13 amino acid coding changes. As mentioned above for the N gene, any of these coding changes may contribute to the observed ts phenotype produced by replacement of the L gene, but several of these coding mutations (shown in italics) are of greater interest because they also differentiate ts11 from its Glasgow progenitor virus, potentially identifying these amino acid substitutions as key contributors to the ts phenotype.

TABLE 4

COMPARISON OF VSV L PROTEIN

| Amino Acid No. | Virus Strain | | |
|---|---|---|---|
| | XN2 | ts11 | Glasgow |
| 87 | Pro | Ser | Ser |
| 88 | Thr | *Ala* | Thr |
| 202 | Ile | Leu | Leu |
| 203 | Arg | Lys | Lys |
| 268 | Tyr | *His* | Tyr |
| 367 | Thr | Ala | Ala |
| 1112 | Pro | *Ser* | Pro |
| 1374 | Ala | Val | Val |
| 1519 | Ile | Leu | Leu |
| 1792 | Leu | Val | Val |
| 1793 | Ile | *Val* | *Ile* |
| 2042 | Leu | Ser | *Leu* |
| 2075 | Arg | Lys | Lys |

G-Stem Mutations and G-Stem/Gene Shuffling Mutations

In certain embodiments, a genetically modified VSV of the invention comprises mutation in the G gene, wherein the encoded G protein has a mutation in the membrane-proximal stem region of the G protein ectodomain, referred to as G-stem protein. The G-stem mutation was introduced by replacing the G gene in the VSV XN vector genetic background (Schnell et al., 1996) with a modified G gene encoding G-stem. G-stem (Robison, 2000) is composed of 108 out of 512 G protein amino acids including: 1) the first 17 amino acids of G protein, which encompasses the signal sequence that targets the polypeptide for membrane insertion; 2) 42 amino acids of the membrane-proximal extracellular domain referred to as the stem; 3) the 20 amino acid membrane-spanning domain; and 4) the 29 amino acid carboxy-terminal intracellular tail. This configuration of the G-stem polypeptide contains sufficient G protein sequence to mediate maturation of viral particles, but lacks sequences necessary to act as a cell attachment protein. Consequently, cells infected with a G-stem vector will express viral proteins and the encoded foreign antigen, but will produce progeny viral particles that are not infectious because the G-stem vector does not encode a fully function G protein.

To produce G-stem vector particles that contain functional G protein needed to infect a target cell, full-length G protein must be provided in trans. This can be accomplished during virus rescue and subsequent vaccine production by one of several procedures: 1) cell lines can be developed that express G protein; 2) a complementing viral vector that expresses G protein can be employed, such as adenovirus, MVA, or VEE; or 3) cells used for production can be transfected with a plasmid DNA vector or mRNA encoding G protein.

Presently, G-stem vector is produced by transient complementation in cells transfected with a plasmid designed to express G protein. This avoids the need to generate cell lines that express G protein, which are difficult to produce because G protein is toxic, and also avoids introduction of a biological reagent like helper-virus into the production process. In some configurations of the G-stem vector, the cistrons encoding viral proteins have been shuffled downstream to permit insertion of a foreign gene into the first genome position. This attenuates the virus and places the foreign antigen gene proximal to the promoter ensuring high levels of expression.

As described above in Section A1, insertion of the HIV gag gene (or any other gene) into the VSV genome at position 1 (3'-gag$_1$-NPMGL-5') effectively results in a gene shuffling mutation, wherein the N, P, M, G and L genes are each moved from their wild-type positions to more distal positions on the genome. Thus, the combination of both the G$_{(stem)}$ mutation and the insertion of gag into the VSV genome at position 1 (gag$_1$), resulted in a doubly mutated genome 3'-gag$_1$-NPMG$_{(stem)}$L5'.

Rescue of Vesicular Stomatitis Viruses in 293 Cells

The successful rescue of VSV from 293 cells was achieved using the basic heat shock/plasmid-T7 system described in international application WO 2004/113517 (specifically incorporated herein by reference), according to the following revised protocol.

Materials

Plasmid DNAs: 1) Full-length viral genomic cDNA, 2) pT7-N, 3) pT7-P, 4) pT7-L, 5) pT7-M, 6) pT7-G and 7) pCl-Neo-bcl-T7 (p0061).

Calcium-phosphate transfection reagents: 1) 2×BES-buffered saline: 50 mM BES (pH 6.95-6.98), 280 mM NaCl, 1.5 mM Na$_2$HPO4, 2) 2-5 M CaCl$_2$ and 3) Hepes-buffered saline wash solution (HBS): 20 mM hepes (pH7.0-7.5), 140 mM KCl, 1 mM MgCl$_2$.

Cell Culture Solutions: 1) DMEM supplemented with 10% certified, heat-inactivated FBS (DMEM/FBS), 2) Iscoves Modified Minimal Essential Medium (IMEM) supplemented with 10% certified, heat-inactivated FBS (IMEM/FBS), 3) Poly-L-Lysine: 0.01% in H$_2$0, 4) PBS and 5) Porcine trypsin/EDTA.

Procedures

293 Cell Culture: 293 cells can be difficult to culture, and there are number of different methods to handle them. The current method has been used successfully as part of a rescue system for VSV and modified VSV vector constructs.

Routine Subculturing:

1) Remove medium and wash the confluent monolayer (10 cm plate) with 5 ml of warm PBS; Pipet gently along the side of the dish to prevent detachment of the cells (293 cells left at room temperature for too long, or in media that become basic (red), will detach).

2) Gently add 2 ml of trypsin and rock the plate to cover the entire monolayer. Aspirate the trypsin and allow the plate to stand at room temperature for about a minute. Tilt the plate on a 45-degree angle and tap it against the working surface of the hood to detach the cells. If the cells do not detach, incubate another minute at room temperature (make sure the cells detach at this stage so that vigorous pipeting can be avoided).

3) Gently add 5 ml of DMEM/FBS and pipet up and down slowly to disperse the cells.

4) Add 1 ml of cells to a plate containing 9 ml of DMEM/FBS.

5) Incubate at 37° C., 5% CO$_2$.

Subculture for Transfection:

1) Coat the desired number of plates with poly-L lysine. Add about 3-4 ml of 0.001% poly-L lysine per plate and allow it to stand at room temperature for at least 30 minutes. Aspirate the poly-L lysine solution. Rinse the plate with 5 ml of medium.

2) Trypsinize the cells as described above. Use a split ratio that will yield a 50-75% confluent plate the following day (1:3 to 1:6).

3) After detaching the cells add IMEM/FBS and transfer the cells to the coated plate containing 9 ml of IMEM/FBS. It seems to be important to split the cells and allow overnight growth in IMEM/FBS before transfection.

4) Incubate at 37° C., 5% CO$_2$.

Transfection:

1) 1-3 hours prior to transfection, feed the cells with 9 ml of IMEM/FBS and incubate the cells in a 32° C. incubator set at 3% CO$_2$.

2) Prepare the calcium-phosphate-DNA transfection mixture as follows:
   a) Combine the following DNAs in a 5 ml polypropylene tube: (i) 8 µg T7-N, (ii) 4 µg T7-P, (iii) 1.2 µg T7 L, (iv) 1.0 µg T7-M, (v) 1.0 µg T7-G (vi) 10 µg of viral genomic cDNA clone and (vii) 10 µg of hCMV-T7 expression vector.
   b) Adjust the volume to a final volume of 450 µl with water.
   c) Add 50 µl 2.5M $CaCl_2$.
   d) While gently vortexing the tube, add 500 µl of 2×BBS then allow the tube to stand at room temperature for 15-20 minutes.

3) Remove the cells from the incubator and slowly add the calcium-phosphate-DNA mixture to the culture medium and swirl gently to distribute the precipitate. Immediately return the cells to the 32° C.-3% $CO_2$ incubator.

4) Three hours after initiating transfection, seal the culture dishes in a plastic bag and fully submerse in a water bath set at 43° C. for 2 hours to induce the cellular heat shock response.

5) After heat shock, return the cells to the 32° C.-3% $CO_2$ incubator and continue incubation overnight.

6) The following day, wash the cells 2 times with HBS and feed the cells with 10 ml of IMEM/FBS. Incubate at 37° C., 5% $CO_2$.

7) At 48-72 hours after initiating transfection, set up sufficient T150 flasks containing 20 ml DMEM/FBS for transfer of transfected cells to the larger vessel. One T150 flask for every 10 cm plate that was transfected.

8) Transfer the transfected 293 cells by gently pipeting the culture medium over the monolayer to dislodge it from the cell surface. Avoid vigorous pipeting and use just enough force to dislodge the cells. After the cells are dislodged, pipet up and down about 5 times to reduce the size of the cell clumps then transfer the medium and cells to a T150 flask containing the 20 ml of IMEM/FBS.

9) Four to 6 hours later, replace the medium with fresh DMEM supplemented with 10% FBS (note that this step can be delayed until 24 hours if the cells are not adhering to the plate. Also, this step has been skipped successfully).

10) Monitor the cells for 5-7 days to detect evidence of cytopathic effect.

11) When CPE appears evident, transfer 50 ul of medium supernatant to well in a six well plate that contains medium and an established Vero cell monolayer. CPE should be visible the following day if rescue has occurred. (Note that this step is important because the 293 cells do at times detach from the surface of the T150 flask and appear VSV-infected when they actually are not).

12) After transferring the small sample to the Vero cell monolayer, harvest the cells and medium from the T150 flask and freeze at −70. The 293 cells can generally be harvested by pipeting the medium over the monolayer to detach the cells.

Rescue of Vesicular Stomatitis Viruses in Vero Cells

Solutions

The following solutions are generally useful for host cell transfection:

1) A 2×BBS (per L) solution (2×BES-buffered saline) of 280 mM NaCl [16.4 g NaCl (or 56 ml 5M NaCl)], 50 mM BES [10.7 g BES (free acid form)], and 1.5 mM sodium phosphate [0.21 g $Na_2HPO_4$]. The BBS solution is adjusted to pH 6.95-6.98 with NaOH. The solution is then filter-sterilized and stored frozen.

2) A 2.5 M $CaCl_2$ solution of 36.8 g per 100 ml total volume is prepared and stored at −20° C. The solution is filter-sterilized using nitrocellulose. Cellulose acetate filters are to be avoided because they clog. Alternatively, the transfection solutions are autoclaved for sterilization. However, the latter procedure may be less desirable, because the 2×BBS solution may change slightly during autoclaving.

The following solutions are generally useful for the medium:

1) A DMEM+FBS solution of DMEM (high glucose with glutamine; Gibco/BRL, [Grand Island, N.Y.]), supplemented with 10% heat-inactivated and certified FBS, and 10-20 μg/ml (optionally up to 50 μg/ml) gentamicin.

2) An MEM+FBS solution of MEM (supplemented with glutamine, nonessential amino acids, 10% heat-inactivated and certified FBS, and 10-20 μg/ml (optionally up to 50 μg/ml) 20-25 mM Hepes buffer; Gibco/BRL) (Grand Island, N.Y.) and optionally including 1× Fungizone).

3) An HBS solution of Hepes-buffered saline wash solution, 20 mM hepes, pH 7.0, 150 mM NaCl, 1 mM $MgCl_2$.

Methods

A generally useful host cell can be selected from split Vero cells, which are placed in DMEM+FBS the day before transfection so they will be approximately 50% confluent [80-90% for RSV] the following day (in six-well plates or 12.5 $cm^2$ flasks). Higher cell densities work less effectively. The following day, each culture is fed 1-4 hours before transfection with 4.5 ml of DMEM+FBS. The cells are then transferred to a $CO_2$ incubator set at 3% $CO_2$ and 32° C. The Vero cells can be grown longer than overnight as long as they are approximately 50% confluent at the time of transfection.

A $CaCl_2$/phosphate precipitate is obtained as follows: BBS and $CaCl_2$ are maintained at room temperature before starting. The DNA mix is prepared in a 5 ml polypropylene tube containing a total volume of 250 μl, with plasmid DNA 2-20 μg total, and 25 μl $CaCl_2$. The DNAs for full-length rescue include 5 μg of a full-length cDNA construct for VSV, 400 ng N protein, 300 ng P protein, 100-200 ng L protein, and 5-10 μg pCl-Neo-Bcl-T7 plasmid (SEQ ID NO: 1; FIG. 2). The efficiency of rescue in Vero cells is low, so 3-6 wells are transfected per full-length construct being rescued.

After all DNA/$CaCl_2$ solutions are prepared, 2×BBS is added. This is usually done by gently agitating a tube by continuous low-speed vortexing and adding 250 μl of 2×BBS dropwise down the side of the tube. This is repeated for all tubes, which are allowed to stand at room temperature for an additional 15-20 minutes to permit the DNA-Calcium-Phosphate precipitate to form. After the room temperature incubation, the precipitate is added dropwise to the cell culture medium and distributed evenly by rocking the plate. The medium is then incubated for three hours in an incubator set at 3% $CO_2$. A level of 3% $CO_2$ is important for the BBS/$CaCl_2$ transfection technique; 5% $CO_2$ works very poorly, if at all. The 3% $CO_2$ controls the pH of the medium and allows formation of an effective calcium-phosphate-DNA precipitate in the medium.

A heat shock procedure is then optionally carried out, for example at three hours after initiation of transfection. The cells are transferred to a water bath set at 44° C. The cells are sealed in a plastic storage bag so the cultures can be fully submersed in water. After three hours at 44° C., the cells are transferred back to a 32° C. incubator set at 3% $CO_2$ and the incubation is continued overnight.

On the following day, the transfection medium is removed and the cells are washed two times with HBS. After washing, 2 ml of fresh DMEM+FBS are added. PBS and Hank's buffer works poorly for the wash step, probably because the phosphate in these buffers causes more $CaCl_2$ to precipitate out of the transfection medium.

A co-culture procedure is then optionally performed. The transfected cells are harvested at 48-72 hours post-transfection by scraping them into the medium and transferring the cells plus medium to a T25 flask that contained a 50% confluent monolayer of Vero cells. Six hours after initiating this co-culture, the medium is replaced with 4 ml of MEM+FBS. The cultures are then incubated for five days. If the medium begins to appear exhausted during this incubation period, 2 ml of media are removed and replaced with fresh MEM+FBS. It is not recommended that all of the media be replaced, in order to conserve any small amount of virus being generated during rescue which may be in the media. During this co-culture phase, CPE may become evident, but this is usually not the case. If no CPE is evident, the rescue can be continued.

The cells are harvested five days after initiating the co-culture. First, 0.5 ml of 2.18M Sucrose, 37.6 mM $KH_2PO_4$, 71.0 mM $K_2HPO_4$, 49.0 mM sodium glutamate are added to the medium and mixed by rocking the flask. Then the cells are scraped into the medium, pipetted up-and-down to mix, and then aliquoted into freezer tubes for shipping and then quick-frozen in a dry-ice/ethanol bath and stored at $-80°$ C.

VSV Vector Purification

Rescued VSV vectors were plaque-purified from the supernatants of transfected cells. After three successive rounds of plaque purifications, virus was amplified on BHK cells to produce a seed stock, which in turn was further amplified on BHK cells to produce a virus working stock. In order to prepare large amounts of virus for animal experiments, the working stock was used to infect 10-20 T-150 flasks of confluent BHK cells, at a multiplicity of infection (MOI) of 0.5-1.0 plaque forming units (pfu)/cell. After 48 hours at 32° C., the infected cell supernatants were clarified by centrifugation at 4,000×g. Virus was then concentrated from the supernatants by centrifugation in a SW 28 rotor at 25,000 rpm for one hour, through a 10% sucrose cushion. Virus pellets were resuspended in phosphate buffered saline (PBS) and snap frozen in an ethanol/dry ice bath. The concentrated virus stock was then titrated on Vero cell monolayers to determine the number of infectious particles in the preparation.

Virus Titration

The number of infectious virus particles in a virus preparation was determined by a standard plaque assay. Briefly, freshly confluent overnight Vero cell monolayers in six-well plates were infected with ten-fold serial dilutions of the virus preparation. To do this, growth medium was aspirated from the cell monolayers and 100 µl aliquots of each virus dilution in DMEM were transferred in triplicate to the center of cell monolayers. To prevent cell desiccation 400 µl of DMEM was then added to each cell monolayer and the plates were held at room temperature for fifteen minutes, followed by thirty minute incubation at 37° C., 5% $CO_2$, with occasional rocking. The virus inoculum was then removed and each cell monolayer was overlaid with 3 ml of 0.8% agarose in DMEM. Plates were then incubated at 37° C., 5% $CO_2$ for 1-4 days to allow plaque formation. The agarose plugs were then removed, and cells were stained with crystal violet (2% crystal violet in 50% methanol) for ten minutes at room temperature. Excess stain was then removed and the cell monolayers were rinsed thoroughly with water. Virus plaques were then visualized in the cell monolayer as small holes that did not stain blue.

Quantitation of Viral RNA by Real Time PCR

A quantitative Real-Time PCR (RT/PCR) assay was used for detection and quantitation of VSV genomes in the tissue of animals. The assay utilizes a 2-step RT/PCR approach that specifically detects the negative sense virus genomic RNA and uses a synthetic oligonucleotide of the entire amplicon for development of a standard curve. Briefly, brain tissues from monkeys, ferrets and mice were homogenized as 20% W/V slurry in SPG. The slurry was centrifuged at 3,000×g for fifteen minutes to pellet particulate matter. The supernatant was then further centrifuged at 14,000×g, and total RNA was extracted from the resulting supernatant. This RNA was used as template for reverse transcription, with virus specific primers, and the products were then used for the Real-Time PCR assay.

Determination of 50% Lethal Dose ($LD_{50}$) of VSV Vectors in Mice

The mouse $LD_{50}$ model was used as a measure of the relative attenuation of the VSV vectors. Several log-fold dilutions of wild-type VSV, 3'-NPMG$_{(ct-1)}$L-5', 3'-PNMG$_{(ct-1)}$L-5', and 3'-PMNG$_{(ct-1)}$L-5' were injected intracranially into four-and-a-half-week-old female Swiss Webster mice (6-10 mice per group). Mice were followed for weight loss, paralysis and death ($LD_{50}$) for three weeks. The $LD_{50}$ was calculated from the cumulative percent mortality by the method of Reed and Muench.

Mouse Immunogenicity Studies

Mice (n=15) were immunized intramuscularly with $1 \times 10^7$ pfu of the indicated VSV vectors (Indiana serotype) set forth in Example 4. Splenocytes from one set of mice ("Prime", n=5) were isolated at the peak of the effector phase 7 days post priming. Two sets of mice (n=10) were boosted with $1 \times 10^7$ pfu of the indicated VSV vector (NJ-G-switch version). Splenocytes from one set of mice ("Boost", n=5) were isolated at the peak of the effector phase 5 days post boosting. Splenocytes from another set of mice (Memory, n=5) were isolated during the memory phase 30 days post boosting. Gag specific CD8 T cell frequencies were determined by tetramer staining. Gag specific IFN-γ secretion was determined by ELISPOT after overnight stimulation with the gag immunodominant peptide.

Example 2

Characterization of VSV Mutants

Figure 2:
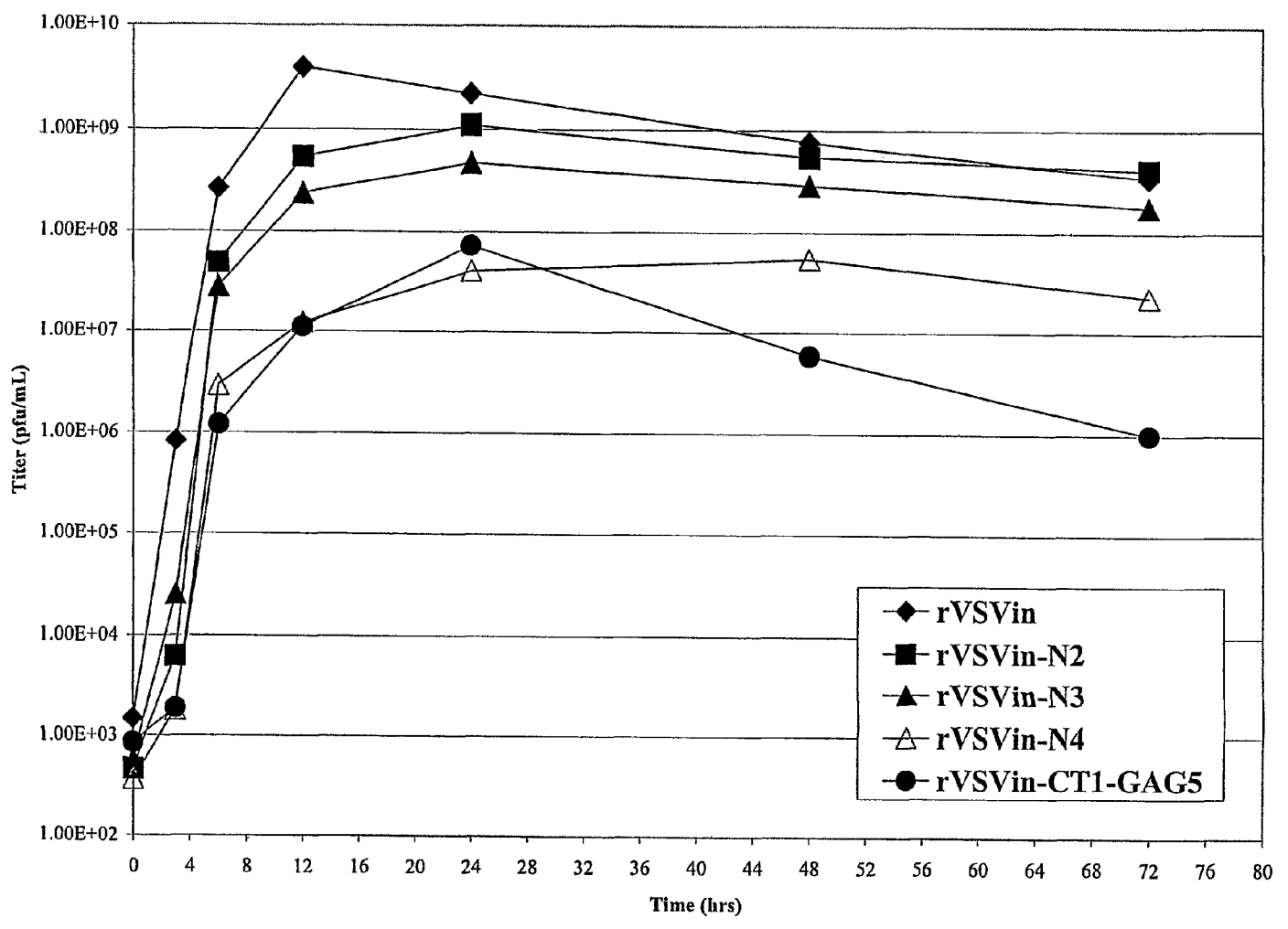
Figure 3:
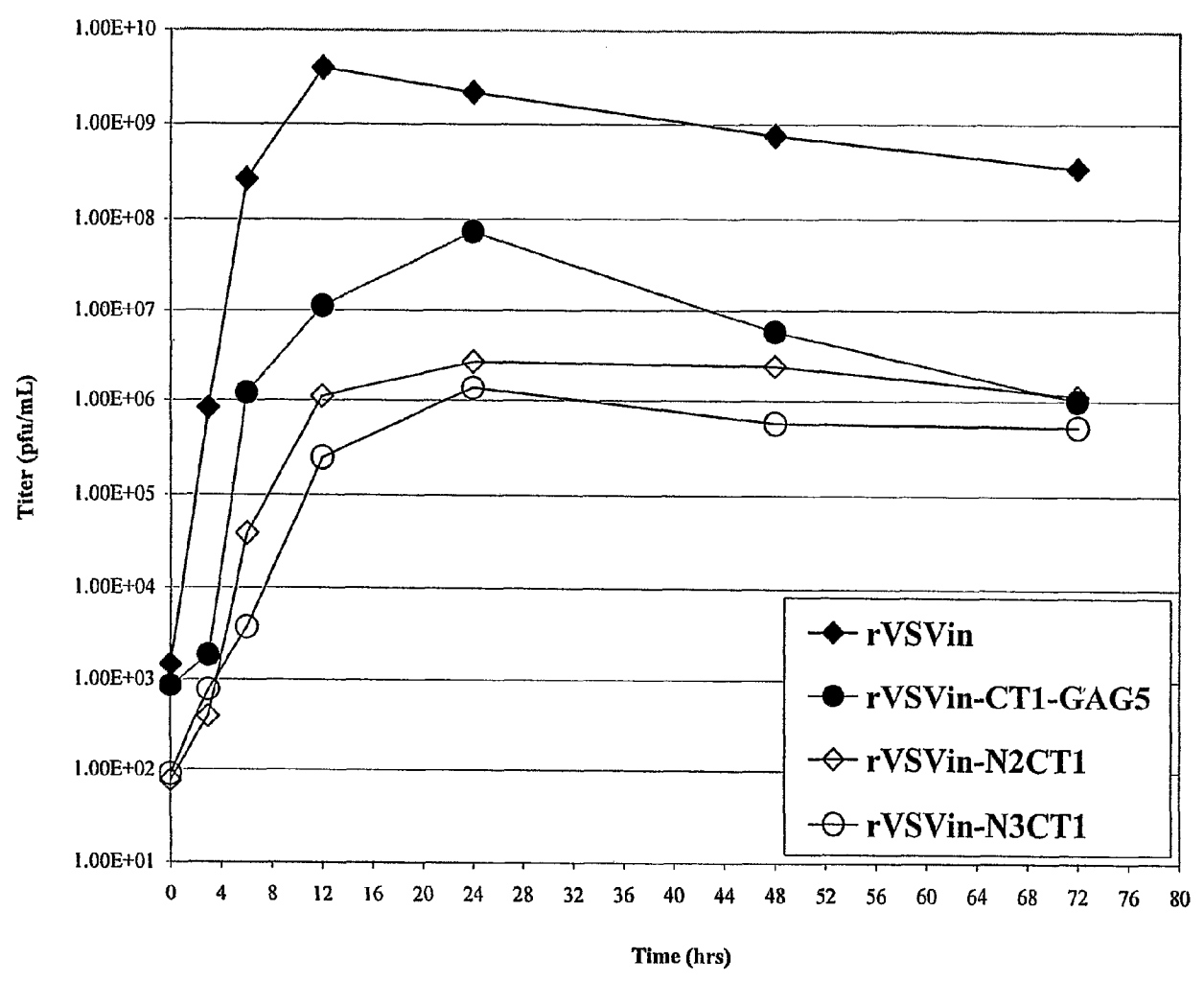

Substantial differences between the plaque sizes of the combined two mutation class VSV vectors described in Example 1 (N shuffled/G protein ct truncation) versus single class mutation VSV vectors were observed (Table 5). Typically, single class mutation VSV vectors formed plaques of countable size in a twenty-four hour plaque assay, while some of the N shuffled/G protein ct truncation vectors required three to four days to form equivalent sized plaques. The relative differences in plaque size for the VSV vectors also paralleled relative differences observed during growth kinetics studies in cell culture (FIG. 1 through FIG. 3).

TABLE 5

RELATIVE PLAQUE SIZE OF VSV VECTORS

| VSV Vector | Plaque Size at 48 hours post infection | |
|---|---|---|
| 3'-NPMGL-5' | 5+ | ● |
| 3'-PMNGL-5' | 3+ | ● |
| 3'-NPMG$_{(ct-1)}$L-5' | 2+ | ● |
| 3'-PNMG$_{(ct-1)}$L-5' | 1+ | ● |

TABLE 5-continued

RELATIVE PLAQUE SIZE OF VSV VECTORS

| VSV Vector | Plaque Size at 48 hours post infection |
|---|---|
| 3'-PMNG$_{(ct-1)}$L-5' | 0.5+ ● |

Example 3

VSV Neurovirulence Studies

The synergistic attenuation of VSV comprising a combination of two or more mutation classes, relative to the single class VSV mutant vectors, was evaluated in a series of mouse, ferret and monkey neurovirulence studies, the methods of which are described in Example 1. Mice are highly permissive for VSV replication and this property allows them to be used to discriminate different levels of virus growth and attenuation. A distinct gradient of pathogenicity/attenuation was observed in mice for the different VSV vectors (Table 6 and Table 7). For example, the LD$_{50}$ in mice inoculated intracranially with 3'-NPMGL-5', 3'-NPMG$_{(ct-1)}$L-5', 3'-PNMG$_{(ct-1)}$L-5' or 3'-PMNG$_{(ct-1)}$ L-5' (Table 6), indicated the following relative attenuation gradient: 3'-PMNG$_{(ct-1)}$L-5' (LD$_{50}$=2×10$^5$)>3'-PNMG$_{(ct-1)}$L-5' (LD$_{50}$=1×10$^4$)>3'-NPMG$_{(ct-1)}$L-5' (LD$_{50}$=14.5)>3'-NPMGL-5' (LD$_{50}$=3.2).

TABLE 6

NUMBER OF MICE DEAD OR PARALYZED

| Vector | IC Dose (pfu) | | | | | |
|---|---|---|---|---|---|---|
| | 1 | 10 | 100 | 1000 | 10000 | 100000 |
| 3'-NPMG$_{(ct-1)}$L-5' (LD$_{50}$ = 14.5 pfu) | ND | 3 Died | 5 Died | 6 Died | 6 Died | ND |
| 3'-PNMG$_{(ct-1)}$L-5' (LD$_{50}$ = 1 × 10$^4$ pfu) | ND | 2 Paralyzed | 3 Died 1 Paralyzed | 1 Died 1 Paralyzed | 1 Died 1 Paralyzed | ND |
| 3'-PMNG$_{(ct-1)}$L-5' (LD$_{50}$ > 2 × 10$^5$ pfu) | ND | ND | 1 Died 1 Paralyzed | 1 Paralyzed | 3 Paralyzed | 2 Died 4 Paralyzed |
| 3'-NPMGL-5' (wt) (LD$_{50}$ = 3.2 pfu) | 1 Died | 5 Died | 6 Died | 6 Died | ND | ND |

6 mice were inoculated intracranially (IC) with each of the vectors above.

The LD$_{50}$ in mice injected intracranially with VSV vectors having zero (wild-type VSV), one, two, three and four (gag gene insertion) mutation classes, shown below in Table 7, also exhibited a similar attenuation gradient. Furthermore, mice injected intracranially with VSV vectors 3'-gag$_1$-PMNG$_{(ct1)}$L-5', 3'-gag$_1$-N$_{(ts)}$PMGL$_{(ts)}$-5, 3'-gag$_1$-NPMGL$_{(ts)}$-5', 3'-gag$_1$-NPM$_{(ncp)}$G$_{(ct1)}$L-5, 3'-gag$_1$-PMNG$_{(ct9)}$L$_{(ts)}$-5' and 3'-gag$_1$-NPMG$_{(stem)}$L-5', exhibited no mortality.

TABLE 7

INTRACRANIAL NEUROVIRULENCE OF VSV VECTORS IN MICE

| Vector | LD$_{50}$ (pfu) | No. of Mutation Classes |
|---|---|---|
| 3'-NPMGL-5' (VSV wt) | 3.2 | 0 |
| 3'-NPMGL-5' (rVSV) | 10 | 0 |
| 3'-NPMG-gag$_5$-L-5' | 10 | 1 |
| 3'-PNMGL-5' | 12 | 1 |
| 3'-PMNGL-5' | 14 | 1 |
| 3'-NPMG$_{(ct-1)}$L-5' | 14.5 | 1 |
| 3'-NPMG$_{(ct-1)}$-gag$_5$-L-5' | 24 | 2 |
| 3'-gag$_1$-NPMGL-5' | 115 | 1 |
| 3'-PNMG$_{(ct-1)}$L-5' | 1 × 10$^4$ | 2 |
| 3'-PMNG$_{(ct-1)}$L-5' | 2 × 10$^5$ | 2 |
| 3'-gag$_1$-PMNG$_{(ct-9)}$L-5' | 1 × 10$^6$ | 3 |
| 3'-gag$_1$-PNMG$_{(ct-1)}$L-5' | 1 × 10$^6$ | 3 |
| 3'-NPM$_{(ncp)}$G-gag$_5$-L-5' | >1 × 10$^6$ | 2 |
| 3'-gag$_1$-N$_{(ts)}$PMGL-5' | 8 × 10$^6$ | 2 |
| 3'-PMNG$_{(ct-1)}$-gag$_5$-L-5' | 1 × 10$^7$ | 3 |
| 3'-NPM$_{(ncp)}$G$_{(ct-1)}$-gag$_5$-L-5' | >1 × 10$^7$ | 3 |
| 3'-gag$_1$-PMNG$_{(ct-1)}$L-5' | >1 × 10$^7$ | 3 |
| 3'-gag$_1$-N$_{(ts)}$PMGL$_{(ts)}$-5' | >1 × 10$^7$ | 3 |
| 3'-gag$_1$-NPMGL$_{(ts)}$-5' | >1 × 10$^7$ | 2 |
| 3'-gag$_1$-NPM$_{(ncp)}$G$_{(ct-1)}$L-5' | >1 × 10$^7$ | 3 |
| 3'-gag$_1$-PMNG$_{(ct-9)}$L$_{(ts)}$-5' | >1 × 10$^7$ | 4 |
| 3'-gag$_1$-NPMG$_{(stem)}$L-5' | >1 × 10$^7$ | 2 |

Histopathology data from Cynomolgus monkeys inoculated intrathalamically with the same series of vectors indicated a very similar gradient of attenuation. Both sets of animal data were further corroborated by results from a series of ferret neurovirulence studies, where infectious virus and levels of genomic RNA present in the brains of intracranially inoculated animals were measured periodically by plaque assay and Real-Time PCR, respectively. Collectively these data demonstrate that the combination of two or more mutation classes possess a level of attenuation that is substantially greater than the single mutation class VSV vectors. The mouse LD$_{50}$ titers strongly indicate there is a powerful synergistic effect on attenuation by combining two different classes of mutation in the same VSV vector.

Example 4

Enhanced Immunogenicity of Attenuated VSV Vectors

The immunogenicity of attenuated VSV vectors 3'-gag$_1$-NPM$_{(ncp)}$G$_{(ct1)}$L-5', 3'-gag$_1$-PMNG$_{(ct9)}$L-5' and 3'-gag$_1$-N$_{(ts)}$PMGL$_{(ts)}$-5' were compared to VSV prototype vectors 3'-NPMG-gag$_5$-L-5' and 3'-NPMGL-5'. Mice were immunized with one of the above VSV vectors, as described in Example 1. The attenuated VSV vectors induced immune responses that were stronger than those induced by the prototype VSV-Gag$_5$ vector (3'-NPMG-gag$_5$-L-5'). Most notable was 3'-gag$_1$-PMNG$_{(ct9)}$L-5', which induced statistically significant higher Gag specific T cell frequencies than were induced by the prototype when assessed after priming and boosting, as well as during the memory phase of the response (Table 8).

TABLE 8

GAG SPECIFIC CD8 T CELL FREQUENCIES

| Vector | Percent Gag Tetramer Positive CD8 T-cells | | |
|---|---|---|---|
| | Prime | Boost | Memory |
| 3'-NPMGL-5' | 0.24 | 0.15 | 0.21 |
| 3'-NPMG-gag$_5$-L-5' | 1.46 | 2.29 | 0.92 |
| 3'-gag$_1$-NPM$_{(ncp)}$G$_{(ct-1)}$L-5' | 0.96 | 3.42 | 2.25 |
| 3'-gag$_1$-PMNG$_{(ct9)}$L-5' | 2.29* | 8.68* | 3.13* |
| 3'-gag$_1$-N$_{(ts)}$PMGL$_{(ts)}$-5' | 0.66 | 3.59 | 0.21 |

*= Response significantly higher than seen for 3'-NPMG-gag$_5$-L-5' (student's t test, p < 0.05).

3'-gag$_1$-PMNG$_{(ct9)}$L-5' also induced IFN-γ secretion that trended higher than induced by the prototype 3'-NPMG-gag$_5$-L-5' (Table 9). Responses to 3'-gag$_1$-NPM$_{(ncp)}$G$_{(ct1)}$L-5' and 3'-gag$_1$-N$_{(ts)}$PMGL$_{(ts)}$-5' also trended higher than those induced by the prototype 3'-NPMG-gag$_5$-L-5' (Table 9).

TABLE 9

GAG IFN-γ ELISPOT

| Vector | IFN-γ Spots per 1 × 10$^6$ Spleen Cells | | |
|---|---|---|---|
| | Prime | Boost | Memory |
| 3'-NPMGL-5' | 0 | 1 | 0 |
| 3'-NPMG-gag$_5$-L-5' | 680 | 887 | 196 |
| 3'-gag$_1$-NPM$_{(ncp)}$G$_{(ct1)}$L-5' | 372 | 984 | 668* |
| 3'-gag$_1$-PMNG$_{(ct9)}$L-5' | 908 | 1,552 | 496 |
| 3'-gag$_1$-N$_{(ts)}$PMGL$_{(ts)}$-5' | 129 | 632 | 413 |

*= Response significantly higher than seen for 3'-NPMG-gag$_5$-L-5' (student's t test, p < 0.05).

Example 5

Immunogenicity of Intramuscular and Intranasal Delivery of Attenuated VSV Vectors Expressing HIV Gag in Rhesus Macaques The following studies are designed to measure the immune responses elicited in Rhesus macaques, following immunization with attenuated VSV vectors expressing HIV gag protein.

The study set forth in Table 10 is performed with a total of twenty-four genetically unselected male rhesus macaques, wherein each group of animals (i.e., Groups 1-6) is immunized either intramuscularly or intranasally with one of the following VSV vectors at a dose of 1×10$^7$ (pfu): 3'-gag$_1$-N$_{(ts)}$PMGL$_{(ts)}$-5' (TsN+L), 3'-gag$_1$-PMNG$_{(ct9)}$L-5' (N4CT9) or 3'-NPMG-gag$_5$-L-5' (Gag5).

The study set forth in Table 11 is performed with a total of twenty-four genetically unselected male rhesus macaques, wherein each group of animals (i.e., Groups 1-8) is immunized either intramuscularly or intranasally with one of the following VSV vectors at a dose of 1×10$^7$ (pfu): 3'-gag$_1$-NPM$_{(ncp)}$G$_{(ct1)}$L-5' (MncpCT1), 3'-gag$_1$-NPMG$_{(stem)}$L-5' (G Stem), 3'-gag$_1$-PMNG$_{(ct1)}$L-5' (N4 CT1) or 3'-NPMG-gag$_5$-L-5' (Gag5).

Generally, the following assays are used to examine systemic and humoral immune responses and VSV shedding from each animal: Cellular Immune Responses: HIV gag peptide specific IFN-γ ELISPOT response and VSV N peptide specific IFN-γ ELISPOT response. Humoral Immune Response: Serum anti-HIV gag antibody titers by ELISA, serum anti-VSV antibody titers by ELISA and serum anti-VSV neutralization antibody titers.

TABLE 10

PRIMATE IMMUNOGENICITY STUDY

| Group | # Animals | Prime (Indiana serotype) | Boost (New Jersey serotype) | Dose | Route |
|---|---|---|---|---|---|
| 1 | 5 | TsN + L | TsN + L | 1 × 10$^7$ | IM |
| 2 | 5 | TsN + L | TsN + L | 1 × 10$^7$ | IN |
| 3 | 5 | N4CT9 | N4CT9 | 1 × 10$^7$ | IM |
| 4 | 5 | N4CT9 | N4CT9 | 1 × 10$^7$ | IN |
| 5 | 2 | Gag 5 | Gag 5 | 1 × 10$^7$ | IM |
| 6 | 2 | Gag 5 | Gag 5 | 1 × 10$^7$ | IN |

Route IM is intramuscular.
Route IN is intranasal.

TABLE 11

PRIMATE IMMUNOGENICITY STUDY

| Group | # Animals | Prime (Indiana serotype) | Boost (New Jersey serotype) | Dose | Route |
|---|---|---|---|---|---|
| 1 | 5 | Mncp CT1 | Mncp CT1 | 1 × 10$^7$ | IM |
| 2 | 5 | Mncp CT1 | Mncp CT1 | 1 × 10$^7$ | IN |
| 3 | 5 | G Stem | G Stem | 1 × 10$^7$ | IM |
| 4 | 5 | G Stem | G Stem | 1 × 10$^7$ | IN |
| 5 | 5 | N4CT1 | N4CT1 | 1 × 10$^7$ | IM |
| 6 | 5 | N4CT1 | N4CT1 | 1 × 10$^7$ | IN |
| 7 | 2 | Gag 5 | Gag 5 | 1 × 10$^7$ | IM |
| 8 | 2 | Gag 5 | Gag 5 | 1 × 10$^7$ | IN |

Route IM is intramuscular.
Route IN is intranasal.

REFERENCES

U.S. Pat. No. 5,258,454
U.S. Pat. No. 5,556,747
U.S. Pat. No. 5,789,166
U.S. Pat. No. 6,391,548
U.S. Pat. No. 5,817,879
U.S. Pat. No. 6,168,943
U.S. Pat. No. 6,596,529
U.S. Pat. No. 6,033,886
U.S. Pat. No. 6,673,572
U.S. Provisional Patent 60/477,389
Ahmed and Lyles, "Identification of a Consensus Mutation in M Protein of Vesicular Stomatitis Virus from Persistently Infected Cells that Affects Inhibition of Host-directed Gene Expression" *Virology*, 237(1): 378-88, 1997.
Atkinson et al., *United States. Annu. Rev. Med.*, 43:451-463, 1992.

Ball et al., "Phenotypic consequences of rearranging the P, M, and G genes of vesicular stomatitis virus" *Journal of virology*, 73(6):4705-4712, 1999.

Bellini et al., *Emerging Infectious Diseases*, 4:29-35, 1998.

Canto et al., "Status Spongiosus Resulting from Intracerebral Infection of Mice with Temperature-Sensitive Mutants of Vesicular Stomatitis Virus", *Br. J. exp. Path.*, 57:321-330, 1976.

Collins et al., *Adv. Virus. Res.*, 54:423-451, 1999.

Collins et al., *Respiratory Syncytial Virus*. In "Field's Virology", 3rd Edition, Lippincott-Raven, 1443-1475, 2001.

Cutts et al., *J. Infectious. Dis.*, 170:S32-S41, 1994.

Evans et al., "Temperature-sensitive mutants of complementation group E of vesicular stomatitis virus New Jersey serotype possess altered NS polypeptides", *Journal of Virology*, 31(2):325-333, 1979.

Finke and Conzelmann, "Ambisense gene expression from recombinant rabies virus: random packaging of positive- and negative-strand ribonucleoprotein complexes into rabies virions", *J. Virol.*, 71:7281-7288, 1997.

Finke and Conzelmann, "Virus promoters determine interference by defective RNAs: selective amplification of mini-RNA vectors and rescue from cDNA by a 3' copy-back ambisense rabies virus", J. Virol., 73: 3818-3825, 1999.

Flamand and Bishop, "Primary In Vivo Transcription of Vesicular Stomatitis Virus and Temperature-Sensitive Mutants of Five Vesicular Stomatitis Virus Complementation Groups", *J. of Virology*, 12(6):1238-1252, 1973.

Flamand and Pringle, "The homologies of spontaneous and temperature-sensitive mutants of vesicular stomatitis virus isolated in chick embryos and BHK-21 cells", *J. Gen. Virol.*, 11:81-85,1971.

Flanagan et al., "Rearrangement of the genes of vesicular stomatitis virus eliminates clinical disease in the natural host: new strategy for vaccine development", *J. Virology*, 75:6107-6114, 2001.

Fredericksen and Whitt, "Attenuation of recombinant vesicular stomatitis viruses encoding mutant glycoproteins demonstrate a critical role for maintaining a high pH threshold for membrane fusion in viral fitness", *Virology*, 240: 349-58, 1997.

Gallione et al., "Nucleotide Sequences of the mRNA's encoding the Vesicular Stomatitis Virus N and NS Proteins", *J. Virol.*, 39:529-535, 1981.

Gopalakrishna and Lenard, "Sequence alterations in temperature-sensitive M-protein mutants (complementation group III) of vesicular stomatitis virus", *Journal of* Virology, 56(3):655-659, 1985.

Griffin, Measles Virus. In "Field's Virology", 3rd Edition, Lippincott-Raven, 1401-1442, 2001.

Harty et al., "A Proline-Rich Motif within the Matrix Protein of Vesicular Stomatitis Virus and Rabies Virus Interacts with WW Domains of Cellular Proteins: Implications for Viral Budding", *J. Virology*, 73(4):2921-2929, 1999.

Holloway et al., "Isolation and characterization of temperature-sensitive mutants of vesicular stomatitis virus", *Virology*, 42(4):917-26, 1970.

Irie et al., "Functional Analysis of Late-Budding Domain Activity Associated with the PSAP Moif within the Vesicular Stomatitis Virus M Protein", *J. Virology*, 78(14):7823-7827, 2004.

Jayakar and Whitt, "Identification of two additional translation products from the matrix (M) gene that contribute to vesicular stomatitis virus Cytopathology", *Journal of Virology*, 76(16):8011-8018, 2002.

Jayakar et al., "Mutations in The PPPY Motif of Vesicular Stomatitis Virus Matrix Protein Reduce Virus Budding by Inhibiting a Late Step in Virion Release", *Journal of Virology*, 74(21):9818-27, 2000.

Jeetendra et al., "The Membrane-Proximal Domain of Vesicular Stomatitis Virus G Protein Functions as a Membrane Fusion Potentiator and Can Induce Hemifusion", *Journal of Virology*, 76(23):12300-11, 2002.

Jeetendra et al., "The Membrane-Proximal Region of Vesicular Stomatitis Virus Glycoprotein G Ectodomain Is Critical for Fusion and Virus Infectivity", *Journal of Virology*, 77(23):12807-18, 2003.

Kapikian et al., *Am. J. Epidemiol.* 4:405-21, 1969.

Kim et al., *Am. J. Epidemiol.* 4:422-34, 1969.

Li et al., "Site-specific mutations in vectors that express antigenic and temperature-sensitive phenotypes of the M gene of vesicular stomatitis virus", *Journal of Virology*, 62(10): 3729-3737, 1988.

Lundh et al., "Non-Lethal Infection of Aminergic Reticular Core Nuerons: Age-Dependent Spread of ts Mutant Vesicular Stomatitis Virus from the Nose", *Journal of Neuropathology and Experimental Neurology*, 47(5):497-506, 1988.

Morita et al., "Phenotypic revertants of temperature-sensitive M protein mutants of vesicular stomatitis virus: sequence analysis and functional characterization", *Journal of Virology*, 61(2):256-263, 1987.

Pringle et al., "Enhanced mutability associated with a temperature-sensitive mutant of vesicular stomatitis virus", *Journal of Virology*, 39(2):377-389, 1981.

Pringle et al., "Isolation and characterization of temperature-sensitive mutants of vesicular stomatitis virus, New Jersey serotype", *Journal of Virology*, 8(6):836-841, 1971.

Pringle, "Genetic Characteristics of Conditional Lethal Mutants of Vesicular Stomatitis Virus Induced by 5-Fluorouracil, 5-Azacytidine, and Ethyl Methane Sulfonate", *Journal of Virology*, 5(5):559-567, 1970.

Printz and Wagner, "Temperature-Sensitive Mutants of Vesicular Stomatitis Virus: Synthesis of Virus Specific Proteins", J. of Virology, 7(5):651-662, 1971.

Rabinowitz et al., "Comparison of Central Nervous System Disease Produced by Wild-Type and Temperature-Sensitive Mutants of Vesicular Stomatitis Virus", *Infection and Immunity*, 13(4):1242-1249, 1976.

Rabinowitz et al., "The Uncoupled Relationship Between the Temperature-Sensitivity and Neurovirulence in Mice of Mutants of Vesicular Stomatitis Virus", *J. gen. Virol*, 35:237-249, 1977.

Roberts et al., "Vaccination with a Recombinant Vesicular Stomatitis Virus Expressing an Influenza Virus Hemagglutinin Provides Complete Protection from Influenza Virus Challenge", *Journal of Virology*, 73:3723-3732, 1999.

Robinson and Whitt, "The Membrane-Proximal Stem Region of Vesicular Stomatitis Virus G Protein Confers Efficient Virus Assembly", *Journal of Virology*, 74(5):2239-2246, 2000.

Rose and Gallione, "Nucleotide Sequences of the mRNA's encoding the Vesicular Stomatitis Virus G and M Proteins Determined from cDNA Clones Containing the Complete Coding Regions", *J. Virol*, 39:519+-528, 1981.

Rose et al., "An Effective Aids Vaccine Based on Live Attenuated Vesicular Stomatitis Virus Recombinants", *Cell*, 106 (5):539-49, 2001.

Rose et al., "Glycoprotein Exchange Vectors Based on Vesicular Stomatitis Virus Allow Effective Boosting and Generation of Neutralizing Antibodies to a Primary Isolate of Human Immunodeficiency Virus Type 1", *Journal of Virology*, 74(23):10903-10, 2000.

Schlehuber and Rose, "Vesicular Stomatitis Virus (VSV) Recombinants Expressing the HIV-1 2F5 Epitope Within the VSV G Protein", Abstract Number 321, AIDS Vaccine 2003, New York, September, 2003.

Schlereth et al., "Successful Mucosal Immunization of Cotton Rats in the Presence of Measles-Specific Antibodies Depends on Degree of Attenuation of Vaccine Vector and Virus Dose", *Journal of General Virology*, 84:2145-2151, 2003.

Schlereth et al., "Successful vaccine-induced seroconversion by single-does immunization in the presence of measles virus-specific material antibodies", *J. Virology*, 74:4652-4657, 2000.

Schnell et al., "Requirement for a Non-Specific Glycoprotein Cytoplasmic Domain Sequence to Drive Efficient Budding of Vesicular Stomatitis Virus", *The EMBO Journal.*, 17(5): 1289-1296, 1998.

Schnell et al., "Foreign glycoproteins expressed from recombinant vesicular stomatitis viruses are incorporated efficiently into virus particles", *Proc. Natl. Acad. Sci., USA*, 93:11359-11365, 1996.

Wagner, "Pathogenicity and Immunogenicity for Mice of Temperature-Sensitive Mutants of Vesicular Stomatitis Virus", *Infection and Immunity*, 10(2):309-315, 1974.

Wertz et al., "Gene rearrangement attenuates expression and lethality of a nonsegmented negative strand RNA virus" *Proc. Natl. Acad. Sci. USA*, 95:3501-3506, 1998.

What is claimed is:

1. A genetically modified vesicular stomatitis virus (VSV) comprising at least two different classes of mutations in the same VSV genome, wherein the VSV comprises a truncated G gene mutation and an N gene shuffling mutation, wherein the two mutations synergistically attenuate VSV pathogenicity.

2. The VSV of claim 1, wherein the pathogenicity is further defined as neurovirulence.

3. The VSV of claim 1, wherein the G protein encoded by the truncated G gene has a deletion of the last twenty or twenty-eight carboxy-terminal amino acids.

4. The VSV of claim 1, wherein the G protein encoded by the truncated G gene has a cytoplasmic tail domain consisting of one or nine amino acids.

5. The VSV of claim 1, wherein the N gene is shuffled to 3'-PNMGL-5' or 3'-PMNGL-5', relative to the wild-type VSV genome 3'-NP GL-5', wherein N is the gene encoding the nucleocapsid protein, P is the gene encoding the phosphoprotein, M is the gene encoding the matrix protein, G is the gene encoding the attachment glycoprotein and L is the gene encoding the RNA-dependent RNA polymerase protein.

6. The VSV of claim 1, comprising a mutated genome selected from the group consisting of 3'-PNMG$_{(ct-1)}$L-5', 3'-PNMG$_{(ct-9)}$L-5', 3'-PMNG$_{(ct-1)}$L-5' and 3'-PMNG$_{(ct-9)}$L-5', wherein N is the gene encoding the nucleocapsid protein, P is the gene encoding the phosphoprotein, M is the gene encoding the matrix protein, G$_{(ct-1)}$ is the gene encoding the attachment glycoprotein having a deletion of the last twenty-eight carboxy-terminal amino acids, G$_{(ct-9)}$ is the gene encoding the attachment glycoprotein having a deletion of the last

SEQUENCE LISTING

```
<160> NUMBER OF SEQ ID NOS: 3

<210> SEQ ID NO 1
<211> LENGTH: 29
<212> TYPE: PRT
<213> ORGANISM: Vesicular stomatitis virus

<400> SEQUENCE: 1

Arg Val Gly Ile His Leu Cys Ile Lys Leu Lys His Thr Lys Lys Arg
1               5                   10                  15

Gln Ile Tyr Thr Asp Ile Glu Met Asn Arg Leu Gly Lys
            20                  25

<210> SEQ ID NO 2
<211> LENGTH: 9
<212> TYPE: PRT
<213> ORGANISM: Vesicular stomatitis virus

<400> SEQUENCE: 2

Arg Val Gly Ile His Leu Cys Ile Lys
1               5

<210> SEQ ID NO 3
<211> LENGTH: 11
<212> TYPE: DNA
<213> ORGANISM: Vesicular Stomatitis Virus

<400> SEQUENCE: 3
tatgaaaaaa a                                                       11
``` twenty carboxy-terminal amino acids and L is the gene encoding the RNA-dependent RNA polymerase protein.

7. The VSV of claim 6, further comprising a third class of mutation in the same VSV genome, wherein the mutation is a ts mutation, an ambisense RNA mutation, a non-cytopathic M gene mutation, a gene deletion mutation, a gene insertion mutation or a point mutation.

8. The VSV of claim 1, wherein the VSV injected intracranially in 4-week old female Swiss-Webster mice has a $LD_{50}$ 100-fold, 1,000-fold, 10,000-fold, or 100,000-fold greater than wild-type VSV injected intracranially in 4-week old female Swiss-Webster mice.

9. The VSV of claim 1, wherein the N gene shuffling mutation results from an insertion of at least one foreign RNA sequence into the VSV genome at position 1.

10. A genetically modified VSV vector comprising the VSV of claim 1, further comprising at least one foreign RNA sequence inserted into or replacing a region of the VSV genome non-essential for replication.

11. The vector of claim 10, wherein the foreign RNA is further defined as an open reading frame (ORF).

12. The vector of claim 10, wherein the foreign RNA is selected from the group consisting of an HIV gene, an HTLV gene, an SIV gene, an RSV gene, a PIV gene, an HSV gene, a CMV gene, an Epstein-Barr virus gene, a Varicella-Zoster virus gene, a mumps virus gene, a measles virus gene, an influenza virus gene, a poliovirus gene, a rhinovirus gene, a hepatitis A virus gene, a hepatitis B virus gene, a hepatitis C virus gene, a Norwalk virus gene, a togavirus gene, an alphavirus gene, a rubella virus gene, a rabies virus gene, a Marburg virus gene, an Ebola virus gene, a papilloma virus gene, a polyoma virus gene, a metapneumovirus gene, a coronavirus gene, a *Vibrio cholerae* gene, a *Streptococcus pneumoniae* gene, a *Streptococcus pyogenes* gene, a *Helicobacter pylori* gene, a *Streptococcus agalactiae* gene, a *Neisseria meningitidis* gene, a *Neisseria gonorrheae* gene, a *Corynebacteria diphtheriae* gene, a *Clostridium tetani* gene, a *Bordetella pertussis* gene, a *Haemophilus* gene, a *Chlamydia* gene, an *Escherichia coli* gene, a gene encoding a cytokine, a gene encoding T-helper epitope, a gene encoding a CTL epitope, a gene encoding an adjuvant and a gene encoding a co-factor.

13. The vector of claim 12, wherein the foreign RNA is an HIV gene selected from the group consisting of gag, env, pol, vif, nef, tat, vpr, rev and vpu.

14. The vector of claim 13, wherein the HIV gene is gag and the mutated genome is 3'-$gag_1$-$PNMG_{(ct-1)}$L-5', 3'-$gag_1$-$PNMG_{(ct-9)}$L-5', 3'-$gag_1$-$PNMG_{(ct-9)}$L-5', 3'-$gag_1$-$PNMG_{(ct-9)}$L-5', 3'-$PNMG_{(ct-1)}$-$gag_5$-L-5', 3'-$PNMG_{(ct-9)}$-$gag_5$-L-5' or 3'-$PNMG_{(ct-9)}$-$gag_5$-L-5'.

15. An immunogenic composition comprising an immunogenic dose of the VSV vector of claim 10.

16. The VSV of claim 9, wherein the foreign RNA sequence is an HIV gene.

17. The VSV of claim 16, wherein the HIV gene is gag.

\* \* \* \* \*

UNITED STATES PATENT AND TRADEMARK OFFICE
CERTIFICATE OF CORRECTION

PATENT NO. : 8,287,878 B2  Page 1 of 1
APPLICATION NO. : 11/547236
DATED : October 16, 2012
INVENTOR(S) : Clarke et al.

It is certified that error appears in the above-identified patent and that said Letters Patent is hereby corrected as shown below:

In the Patent

Column    Line
  42       19

Replace "3'-NP GL-5'" with --3'-NPMGL-5'--

Signed and Sealed this
First Day of January, 2013

David J. Kappos
*Director of the United States Patent and Trademark Office*